(12) United States Patent
Bonutti

(10) Patent No.: US 8,062,241 B2
(45) Date of Patent: *Nov. 22, 2011

(54) MYOFASCIAL STRAP

(75) Inventor: Peter M. Bonutti, Effingham, IL (US)

(73) Assignee: Bonutti Research Inc, Effingham, IL (US)

( * ) Notice: Subject to any disclaimer, the term of this patent is extended or adjusted under 35 U.S.C. 154(b) by 385 days.

This patent is subject to a terminal disclaimer.

(21) Appl. No.: 11/248,406

(22) Filed: Oct. 12, 2005

(65) Prior Publication Data

US 2006/0036205 A1     Feb. 16, 2006

Related U.S. Application Data

(63) Continuation of application No. 10/439,418, filed on May 16, 2003, now Pat. No. 6,958,048, which is a continuation of application No. 09/738,791, filed on Dec. 15, 2000, now Pat. No. 6,575,926.

(51) Int. Cl.
*A61F 5/00* (2006.01)
*A61F 13/00* (2006.01)

(52) U.S. Cl. .............. 602/4; 602/75; 128/875; 128/876

(58) Field of Classification Search .............. 602/41–43, 602/46, 20, 21, 74–79, 23, 4, 60–64; 606/201–203; 128/101.1, 865, 875, 876; 2/311, 312, 338
See application file for complete search history.

(56) References Cited

U.S. PATENT DOCUMENTS

| | | |
|---|---|---|
| 432,327 A | 7/1890 | Page |
| 433,227 A | 7/1890 | Beacock |
| 2,191,283 A | 2/1940 | Longfellow |
| 2,206,902 A | 7/1940 | Kost |
| 2,223,276 A | 11/1940 | Ward |
| 2,237,252 A | 4/1941 | Longfellow |
| 2,246,689 A | 6/1941 | Kost |
| 2,250,493 A | 7/1941 | Milne |
| 2,590,729 A | 3/1952 | Scognamillo |
| 2,590,739 A | 3/1952 | Wahner et al. |
| 2,811,154 A | 10/1957 | Scholl |

(Continued)

FOREIGN PATENT DOCUMENTS

CA     2066151     10/1992

(Continued)

OTHER PUBLICATIONS

Advertising materials from the Internet on Jun. 5, 1998 entitled: "Quadrant by Smith & Nephew DonJoy". "Entering a New Plane".

(Continued)

*Primary Examiner* — Kim Lewis

(74) *Attorney, Agent, or Firm* — Armstrong Teasdale LLP

(57) ABSTRACT

An improved strap has a first end portion, a second end portion, and a middle portion extending between the first and second end portions. An inner surface of the middle portion and inner and outer surfaces of the first end portion include a foam material. The foam material of the inner surfaces of the middle and first end portions is positionable against skin of the patient. An outer surface of the middle portion includes a fabric material and a foam region. An inner surface of the second end portion includes a retainer for connecting the inner surface of the second end portion to the fabric material of the outer surface of the middle portion.

50 Claims, 10 Drawing Sheets

U.S. PATENT DOCUMENTS

| | | |
|---|---|---|
| 2,820,455 A | 1/1958 | Hall |
| 2,829,562 A | 4/1958 | La Rue |
| 2,832,334 A | 4/1958 | Whitelaw |
| 3,083,708 A | 4/1963 | Gottfried |
| 3,338,237 A | 8/1967 | Sconce |
| 3,351,055 A | 11/1967 | Gottfried |
| 3,548,818 A | 12/1970 | Kaplan |
| 3,580,248 A | 5/1971 | Larson |
| 3,698,389 A | 10/1972 | Guedel |
| 3,701,349 A | 10/1972 | Larson |
| 3,724,452 A | 4/1973 | Nitschke |
| 3,760,056 A | 9/1973 | Rudy |
| 3,795,243 A | 3/1974 | Miller |
| 3,811,434 A | 5/1974 | Jacobson et al. |
| 3,814,419 A | 6/1974 | Bjorklund et al. |
| 3,856,004 A | 12/1974 | Cox |
| 3,955,565 A | 5/1976 | Johnson, Jr. |
| 3,970,316 A | 7/1976 | Westmoreland, Jr. |
| 3,976,057 A | 8/1976 | Barclay |
| 4,039,183 A | 8/1977 | Sakurada |
| 4,076,022 A | 2/1978 | Walker |
| 4,084,267 A | 4/1978 | Zadina |
| 4,108,170 A * | 8/1978 | Spann ........................ 128/876 |
| 4,180,870 A | 1/1980 | Radulovic et al. |
| 4,214,577 A | 7/1980 | Hoy |
| 4,229,001 A | 10/1980 | Roman |
| 4,237,873 A | 12/1980 | Terry et al. |
| 4,241,731 A | 12/1980 | Pauley |
| 4,273,113 A | 6/1981 | Hofstein |
| 4,285,773 A | 8/1981 | Taciuk |
| 4,320,748 A | 3/1982 | Racette et al. |
| 4,331,144 A * | 5/1982 | Wapner .................... 128/207.17 |
| 4,363,481 A | 12/1982 | Erickson |
| 4,370,977 A | 2/1983 | Mauldin et al. |
| 4,383,523 A | 5/1983 | Schurman |
| 4,396,013 A * | 8/1983 | Hasslinger .................... 128/845 |
| 4,417,569 A | 11/1983 | Brudny |
| 4,433,682 A | 2/1984 | Badra |
| 4,441,489 A | 4/1984 | Evans et al. |
| 4,454,871 A | 6/1984 | Mann et al. |
| 4,456,001 A | 6/1984 | Pescatore |
| 4,456,002 A | 6/1984 | Barber et al. |
| 4,502,470 A | 3/1985 | Kiser et al. |
| 4,502,681 A | 3/1985 | Blomqvist |
| 4,508,111 A | 4/1985 | Hepburn |
| 4,509,509 A | 4/1985 | Bouvet et al. |
| 4,538,595 A | 9/1985 | Hajianpour |
| 4,538,600 A | 9/1985 | Hepburn |
| 4,549,653 A | 10/1985 | Lauritzen |
| 4,570,619 A | 2/1986 | Gamm |
| 4,576,151 A | 3/1986 | Carmichael et al. |
| 4,589,406 A | 5/1986 | Florek |
| 4,606,542 A | 8/1986 | Segal |
| 4,612,919 A | 9/1986 | Best |
| 4,628,913 A | 12/1986 | Lerman |
| 4,641,639 A | 2/1987 | Padilla |
| 4,653,479 A | 3/1987 | Maurer |
| 4,664,106 A | 5/1987 | Snedeker |
| 4,665,905 A | 5/1987 | Brown |
| 4,693,239 A | 9/1987 | Clover, Jr. |
| 4,716,889 A | 1/1988 | Saringer |
| 4,718,665 A | 1/1988 | Airy et al. |
| 4,727,865 A | 3/1988 | Hill-Byrne |
| 4,739,334 A | 4/1988 | Soref |
| 4,744,355 A | 5/1988 | Faasse, Jr. |
| 4,765,320 A | 8/1988 | Lindemann et al. |
| 4,788,941 A | 12/1988 | Villeneuve |
| 4,790,301 A | 12/1988 | Silfverskiold |
| 4,793,334 A | 12/1988 | McGuinness et al. |
| 4,805,601 A | 2/1989 | Eischen, Sr. |
| 4,807,601 A | 2/1989 | Wright |
| 4,809,688 A | 3/1989 | Aymerica del Valle et al. |
| 4,834,073 A | 5/1989 | Bledsoe et al. |
| 4,844,094 A | 7/1989 | Grim |
| 4,844,454 A | 7/1989 | Rogers |
| 4,844,455 A | 7/1989 | Funkhouser, Jr. |
| 4,848,326 A | 7/1989 | Lonardo |
| 4,862,877 A | 9/1989 | Barber |
| 4,865,024 A | 9/1989 | Hensley et al. |
| 4,869,267 A | 9/1989 | Grim et al. |
| 4,869,499 A | 9/1989 | Schiraldo |
| 4,884,454 A | 12/1989 | Johnson |
| 4,884,563 A | 12/1989 | Sessions |
| 4,913,135 A | 4/1990 | Mattingly |
| 4,913,755 A | 4/1990 | Grim |
| 4,930,497 A | 6/1990 | Saringer |
| 4,948,117 A | 8/1990 | Burke |
| 4,953,543 A | 9/1990 | Grim et al. |
| 4,955,369 A | 9/1990 | Bledsoe et al. |
| 4,955,396 A | 9/1990 | Fralick et al. |
| 4,957,281 A | 9/1990 | Christolear, Jr. |
| 4,964,402 A | 10/1990 | Grim et al. |
| 4,991,234 A | 2/1991 | Greenberg |
| 4,996,979 A | 3/1991 | Grim et al. |
| 5,005,563 A | 4/1991 | Veale |
| 5,018,514 A | 5/1991 | Grood et al. |
| 5,019,050 A | 5/1991 | Lynn et al. |
| 5,025,782 A | 6/1991 | Salerno |
| 5,027,688 A | 7/1991 | Suzuki et al. |
| 5,027,801 A | 7/1991 | Grim |
| 5,027,802 A | 7/1991 | Donohue |
| 5,036,837 A | 8/1991 | Mitchell et al. |
| 5,036,838 A | 8/1991 | Sherman |
| 5,052,375 A | 10/1991 | Stark et al. |
| 5,060,662 A | 10/1991 | Farnswoth, III |
| 5,066,299 A | 11/1991 | Bellingham |
| 5,070,866 A | 12/1991 | Alexander et al. |
| 5,078,128 A | 1/1992 | Grim et al. |
| 5,088,481 A | 2/1992 | Darby |
| 5,100,403 A | 3/1992 | Hotchkiss et al. |
| 5,102,411 A | 4/1992 | Hotchkiss et al. |
| 5,116,359 A | 5/1992 | Moore |
| 5,125,400 A | 6/1992 | Johnson, Jr. |
| 5,135,470 A | 8/1992 | Reeves |
| 5,139,475 A | 8/1992 | Robicsek |
| 5,141,489 A | 8/1992 | Sereboff |
| 5,156,589 A | 10/1992 | Langen et al. |
| 5,163,451 A | 11/1992 | Grellas |
| 5,167,612 A | 12/1992 | Bonutti |
| 5,191,903 A | 3/1993 | Donohue |
| 5,197,942 A | 3/1993 | Brady |
| 5,201,702 A | 4/1993 | Mars |
| 5,201,772 A | 4/1993 | Maxwell |
| 5,203,321 A | 4/1993 | Donovan et al. |
| 5,211,161 A | 5/1993 | Stef |
| 5,213,094 A | 5/1993 | Bonutti |
| 5,213,095 A | 5/1993 | Dague |
| 5,218,954 A | 6/1993 | van Bemmelen |
| 5,226,245 A | 7/1993 | Lamont |
| 5,232,435 A | 8/1993 | Leibinsohn |
| 5,235,975 A * | 8/1993 | Gang et al. .................... 607/108 |
| 5,252,101 A | 10/1993 | Rosenwinkel et al. |
| 5,252,102 A | 10/1993 | Singer et al. |
| 5,261,125 A | 11/1993 | Cartwright et al. |
| 5,277,695 A | 1/1994 | Johnson, Jr. et al. |
| 5,285,773 A | 2/1994 | Bonutti et al. |
| 5,297,540 A | 3/1994 | Kaiser et al. |
| 5,312,322 A | 5/1994 | Santana |
| 5,316,022 A | 5/1994 | Schiek, Sr. |
| 5,323,435 A | 6/1994 | Baversten |
| RE34,661 E | 7/1994 | Grim |
| 5,327,882 A | 7/1994 | Saringer et al. |
| 5,328,448 A | 7/1994 | Gray, Sr. |
| 5,329,705 A | 7/1994 | Grim et al. |
| 5,348,530 A | 9/1994 | Grim et al. |
| 5,349,956 A | 9/1994 | Bonutti |
| 5,352,216 A | 10/1994 | Shiono et al. |
| 5,354,260 A | 10/1994 | Cook |
| 5,364,323 A | 11/1994 | Liu |
| 5,365,947 A | 11/1994 | Bonutti |
| 5,370,133 A | 12/1994 | Darby et al. |
| 5,372,597 A | 12/1994 | Hotchkiss et al. |
| 5,376,091 A | 12/1994 | Hotchkiss et al. |
| 5,378,223 A | 1/1995 | Grim et al. |
| 5,385,536 A | 1/1995 | Burkhead et al. |
| 5,389,065 A | 2/1995 | Johnson, Jr. |
| 5,391,132 A | 2/1995 | Greenwald |

| | | | | | | |
|---|---|---|---|---|---|---|
| 5,395,303 A | 3/1995 | Bonutti et al. | 6,184,797 B1 | 2/2001 | Stark et al. | |
| 5,399,152 A | 3/1995 | Habermeyer et al. | 6,228,044 B1 | 5/2001 | Jensen et al. | |
| 5,403,265 A | 4/1995 | Berguer et al. | 6,267,742 B1 | 7/2001 | Krivosha et al. | |
| 5,407,420 A | 4/1995 | Bastyr et al. | 6,296,595 B1 | 10/2001 | Stark et al. | |
| 5,407,422 A | 4/1995 | Matthijs et al. | 6,349,414 B1 | 2/2002 | Tillman | |
| 5,417,643 A | 5/1995 | Taylor | 6,371,123 B1 | 4/2002 | Stark et al. | |
| 5,419,757 A | 5/1995 | Daneshvar | 6,384,755 B1 | 5/2002 | Hayden | |
| 5,421,874 A | 6/1995 | Pearce | 6,409,691 B1 | 6/2002 | Dakin et al. | |
| 5,435,009 A | 7/1995 | Schild et al. | 6,436,058 B1 | 8/2002 | Krahner et al. | |
| 5,437,611 A | 8/1995 | Stern | 6,485,447 B1 | 11/2002 | Lavery et al. | |
| 5,452,205 A | 9/1995 | Telepko | 6,502,577 B1 | 1/2003 | Bonutti | |
| 5,453,075 A | 9/1995 | Bonutti et al. | 6,503,213 B2 | 1/2003 | Bonutti | |
| 5,453,082 A | 9/1995 | Lamont | 6,509,659 B1 | 1/2003 | Carroll et al. | |
| 5,456,268 A | 10/1995 | Bonutti | 6,572,571 B2 | 6/2003 | Lowe | |
| 5,456,286 A | 10/1995 | Warner et al. | 6,573,419 B2 | 6/2003 | Naimer | |
| 5,464,385 A | 11/1995 | Grim | 6,575,926 B2 * | 6/2003 | Bonutti | 602/75 |
| 5,466,213 A | 11/1995 | Hogan et al. | 6,599,255 B2 | 7/2003 | Zhang | |
| 5,466,250 A | 11/1995 | Johnson, Jr. et al. | 6,599,263 B1 | 7/2003 | Bonutti et al. | |
| 5,472,407 A | 12/1995 | Schenck | 6,637,429 B2 | 10/2003 | Mundrick et al. | |
| 5,492,133 A | 2/1996 | McVicker | 6,682,497 B2 | 1/2004 | Jensen et al. | |
| 5,503,619 A | 4/1996 | Bonutti | 6,743,187 B2 | 6/2004 | Solomon | |
| 5,503,622 A | 4/1996 | Wehr | 6,770,047 B2 | 8/2004 | Bonutti | |
| 5,503,908 A | 4/1996 | Faass | 6,890,285 B2 | 5/2005 | Rahman et al. | |
| 5,518,009 A | 5/1996 | Ruiz-Gonzalez | 6,921,377 B2 | 7/2005 | Bonutti | |
| 5,520,181 A | 5/1996 | Kreidler et al. | 6,924,411 B2 | 8/2005 | Reider | |
| 5,520,628 A | 5/1996 | Wehr | 6,929,616 B2 | 8/2005 | Bonutti et al. | |
| 5,527,269 A | 6/1996 | Reithofer | 6,958,048 B2 | 10/2005 | Bonutti | |
| 5,531,669 A | 7/1996 | Varnau | 6,974,431 B2 | 12/2005 | Jensen | |
| 5,535,274 A | 7/1996 | Braitberg et al. | 7,112,179 B2 | 9/2006 | Bonutti et al. | |
| 5,538,486 A | 7/1996 | France et al. | 7,182,738 B2 | 2/2007 | Bonutti et al. | |
| 5,538,500 A | 7/1996 | Peterson | 7,204,814 B2 | 4/2007 | Zalman | |
| 5,571,077 A | 11/1996 | Klearman et al. | 7,306,573 B2 | 12/2007 | Bonutti | |
| 5,577,998 A | 11/1996 | Johnson, Jr. et al. | 7,404,804 B2 | 7/2008 | Bonutti | |
| 5,605,535 A | 2/1997 | Lepage | 7,854,716 B2 | 12/2010 | Schuren et al. | |
| 5,609,570 A | 3/1997 | Lamont | 2001/0047209 A1 | 11/2001 | Solomon | |
| 5,611,764 A | 3/1997 | Bonutti et al. | 2002/0029784 A1 | 3/2002 | Stark | |
| 5,620,411 A | 4/1997 | Schumann et al. | 2002/0183655 A1 | 12/2002 | Zhang | |
| 5,626,537 A | 5/1997 | Danyo et al. | 2004/0153010 A1 | 8/2004 | Bonutti | |
| 5,643,315 A | 7/1997 | Daneshvar | 2004/0215120 A1 | 10/2004 | Jensen | |
| 5,647,378 A | 7/1997 | Farnum | 2006/0036205 A1 | 2/2006 | Bonutti | |
| 5,653,680 A | 8/1997 | Cruz | 2007/0038161 A1 | 2/2007 | Bonutti et al. | |
| 5,665,059 A | 9/1997 | Klearman et al. | 2007/0055190 A1 | 3/2007 | Bonutti et al. | |
| 5,681,269 A | 10/1997 | Basaj et al. | 2007/0100267 A1 | 5/2007 | Bonutti et al. | |
| 5,685,830 A | 11/1997 | Bonutti | 2007/0135738 A1 | 6/2007 | Bonutti et al. | |
| 5,755,679 A | 5/1998 | Selner et al. | 2007/0197605 A1 | 8/2007 | Glombik et al. | |
| 5,761,834 A | 6/1998 | Grim et al. | 2007/0219475 A1 | 9/2007 | Bonutti et al. | |
| 5,772,619 A | 6/1998 | Corbett | 2007/0219476 A1 | 9/2007 | Bonutti et al. | |
| 5,778,565 A | 7/1998 | Holt et al. | 2008/0039759 A1 | 2/2008 | Holm et al. | |
| 5,788,659 A | 8/1998 | Haas | 2008/0091132 A1 | 4/2008 | Bonutti | |
| 5,792,084 A | 8/1998 | Wilson et al. | 2008/0188356 A1 | 8/2008 | Bonutti | |
| 5,820,577 A | 10/1998 | Taylor | 2008/0226700 A1 | 9/2008 | Cozzolino | |
| 5,823,975 A | 10/1998 | Stark et al. | | | | |
| 5,830,170 A | 11/1998 | Whiteman et al. | | FOREIGN PATENT DOCUMENTS | | |
| 5,833,639 A | 11/1998 | Nunes et al. | CA | 2065669 | 10/1993 | |
| 5,839,139 A | 11/1998 | Fink | DE | 8806231.7 | 5/1988 | |
| 5,848,979 A | 12/1998 | Bonutti et al. | EP | 0181668 | 5/1986 | |
| 5,865,773 A | 2/1999 | Koledin | EP | 0181688 | 5/1986 | |
| 5,882,320 A | 3/1999 | Peterson | EP | 0380060 | 1/1990 | |
| 5,882,323 A | 3/1999 | Belkin | EP | 0510840 | 10/1992 | |
| 5,919,148 A | 7/1999 | Marko et al. | FR | 2661333 | 4/1990 | |
| 5,929,782 A | 7/1999 | Stark et al. | JP | 4261657 | 9/1992 | |
| 5,939,399 A | 8/1999 | Vertesy et al. | JP | 2001 087296 | 4/2001 | |
| 5,940,992 A | 8/1999 | Darby | SU | 1158195 | 5/1985 | |
| 5,943,705 A | 8/1999 | Sink | SU | 1426580 | 9/1988 | |
| 5,980,435 A | 11/1999 | Joutras et al. | WO | WO 88/04543 | 6/1988 | |
| 6,007,500 A | 12/1999 | Quintinskie, Jr. | WO | WO 2004/073143 | 1/2004 | |
| 6,018,092 A | 1/2000 | Dunshee | WO | WO 2005/086741 | 9/2005 | |
| 6,021,780 A | 2/2000 | Darby | WO | WO 2007/051168 | 5/2007 | |
| 6,027,468 A | 2/2000 | Pick | WO | WO 2007/109638 | 9/2007 | |
| 6,053,169 A | 4/2000 | Hunt | WO | WO 2008/036895 | 8/2008 | |
| 6,059,576 A | 5/2000 | Brann | | | | |
| 6,093,162 A | 7/2000 | Fairleigh et al. | | OTHER PUBLICATIONS | | |
| 6,099,489 A | 8/2000 | Herzberg et al. | | | | |
| 6,113,562 A | 9/2000 | Bonutti et al. | | | | |
| 6,142,964 A | 11/2000 | Gilmour | | | | |
| 6,142,965 A | 11/2000 | Mathewson | | | | |
| 6,155,994 A | 12/2000 | Hubbard et al. | | | | |
| 6,179,747 B1 | 1/2001 | Kelley | | | | |
| 6,179,800 B1 | 1/2001 | Torrens | | | | |

Advertising materials from the Internet on Jun. 5, 1998 entitled: "Make DonJoy's Quadrant Your First Choice for Effective Post-Operative Shoulder Treatment". "Quadrant Brace Specifications".
Advertising materials from the Internet on Jun. 5, 1998 entitled: "Ultraslingtm by DonJoy".
Neporent et al. "Weight Training for Dummies" 1997, p. 294.

Dynasplint Systems Inc., "Practitioner Information for Dynasplint LPS Orthosis-Knee Extension", date known but prior to Aug. 23, 1991.

Publication by UE Tech, Technology Meeting Human Needs, Rehabilitation Product Catalog, vol. 7, publication date unknown, but prior to Oct. 13, 1998.

Taber's Cyclopedic Medical Dictionary 16th Edition (1989) (#34), p. 521, definition of "distraction".

Health Enterprises, Inc., ACU-Life 306 Hot & Cold Universal Therapy Brace, www.healthenterprises.com, 2011, 1 page.

* cited by examiner

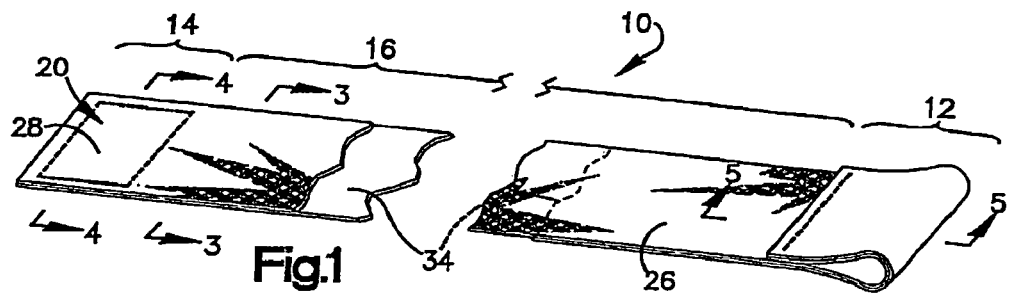
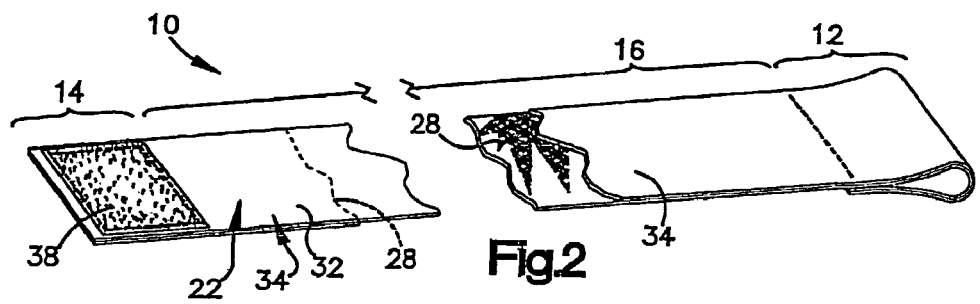
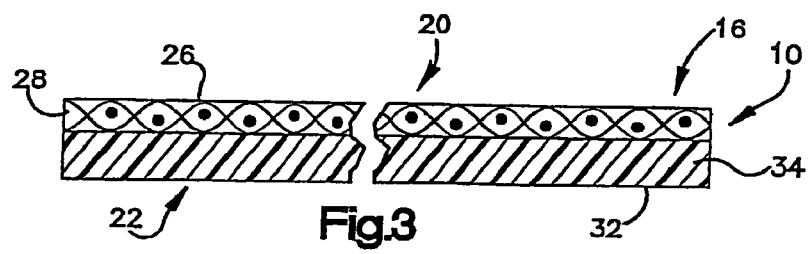
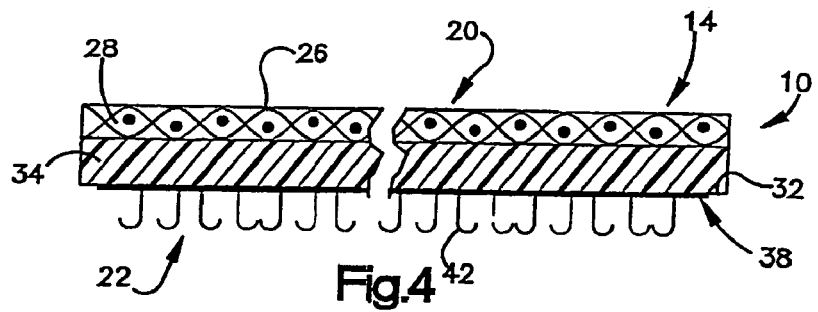

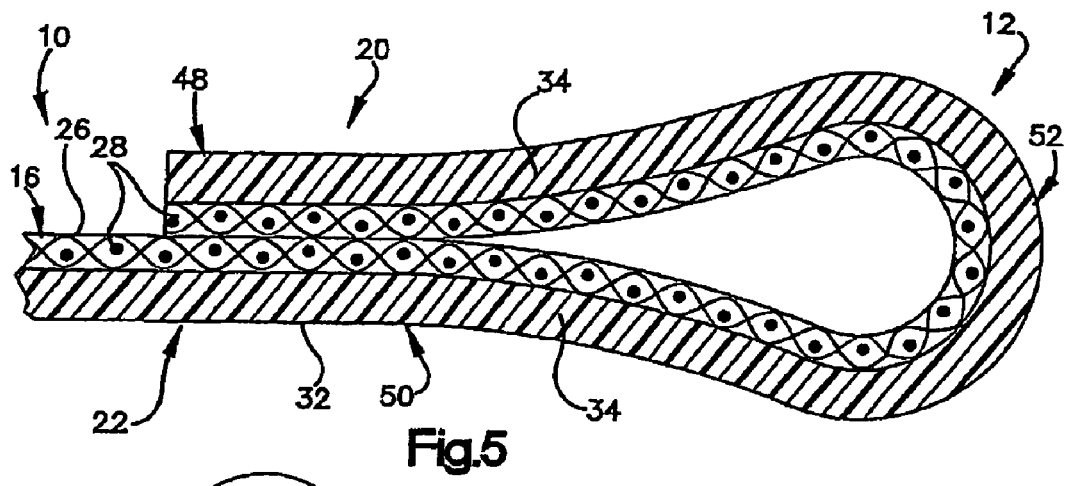
Fig.5
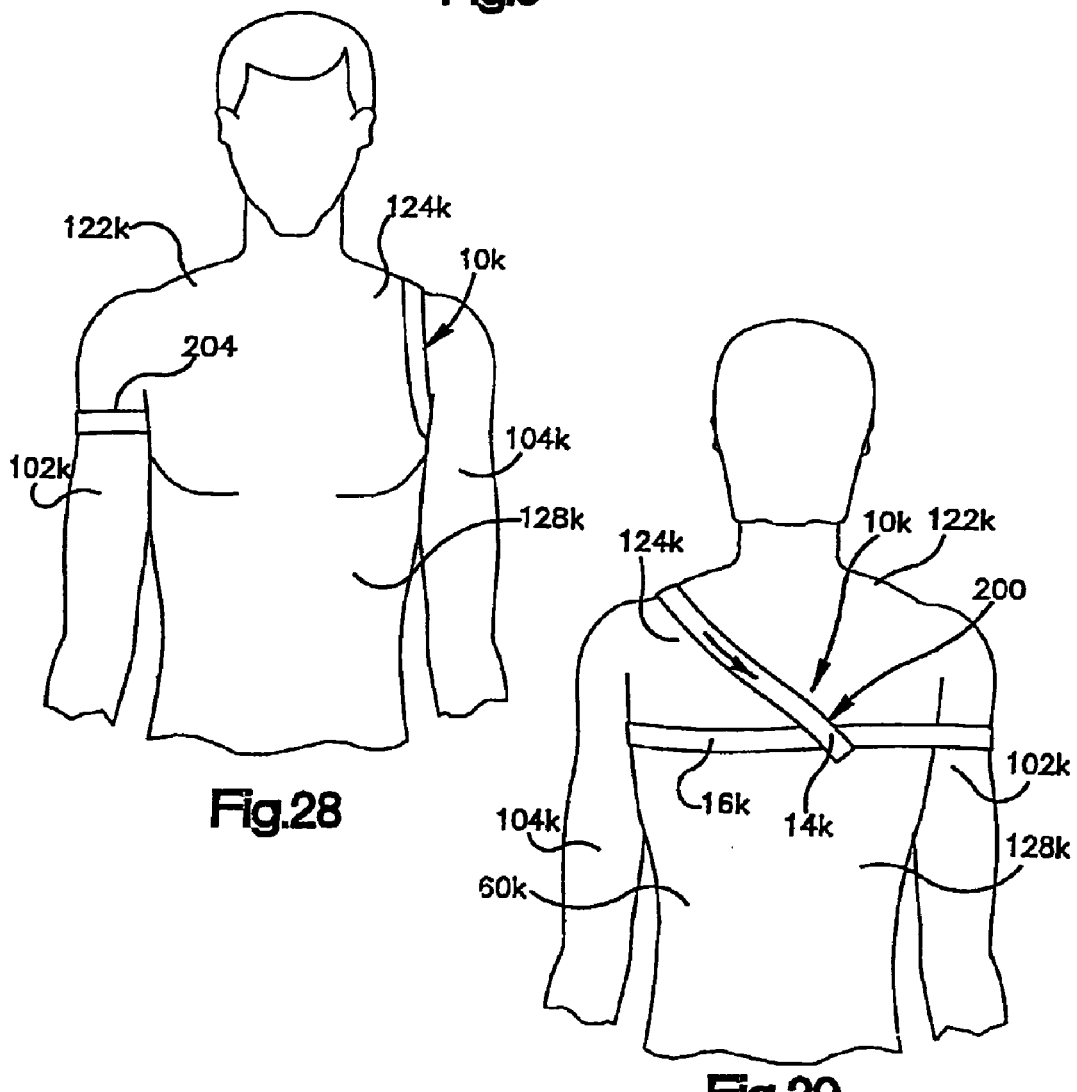
Fig.28
Fig.29

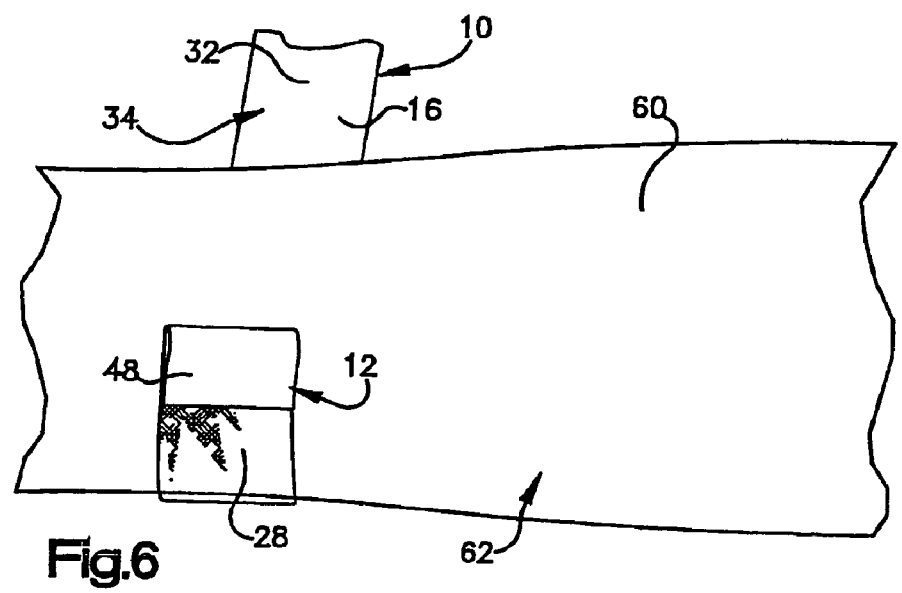
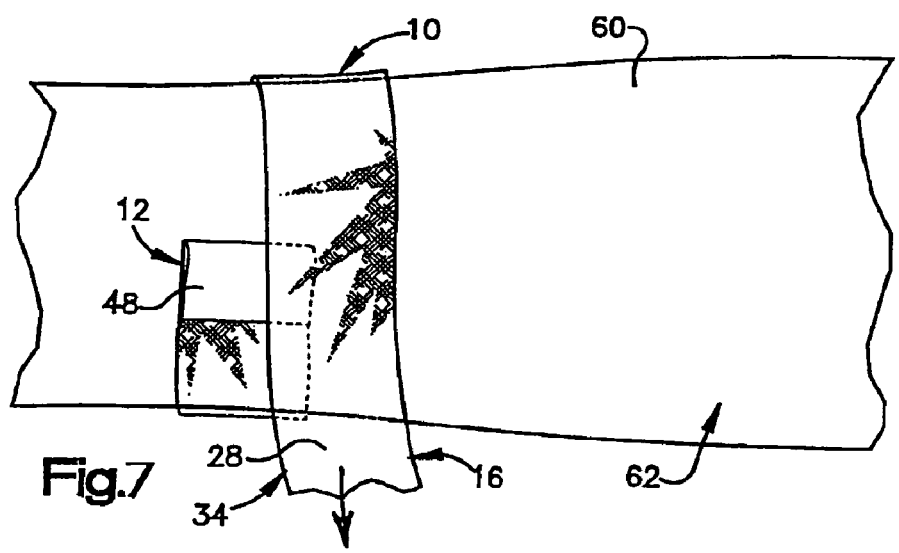
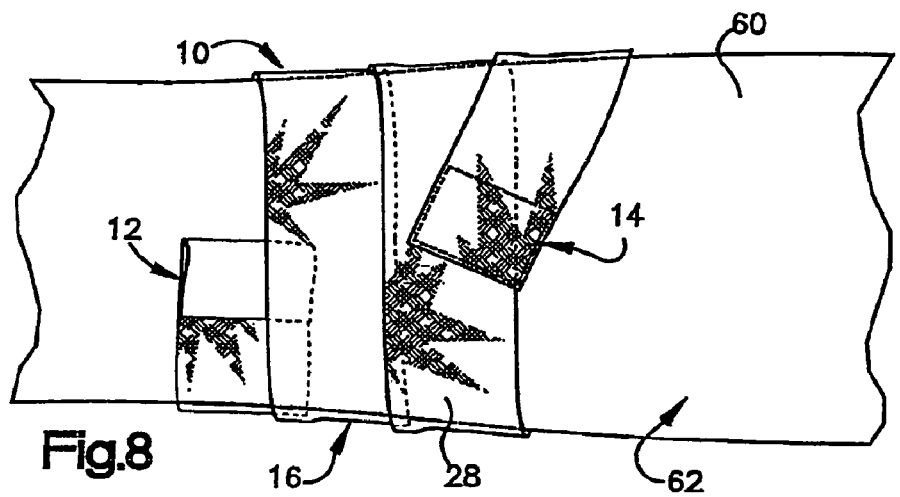

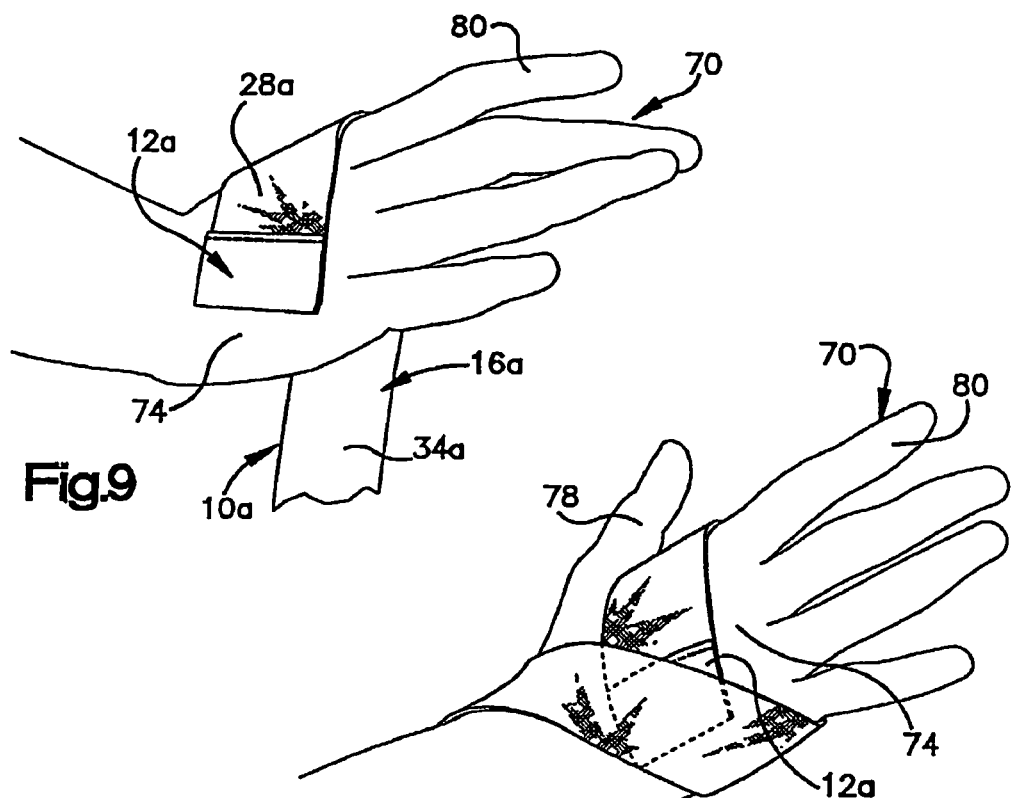
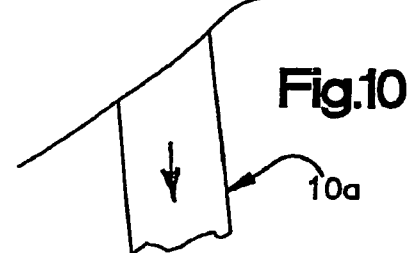
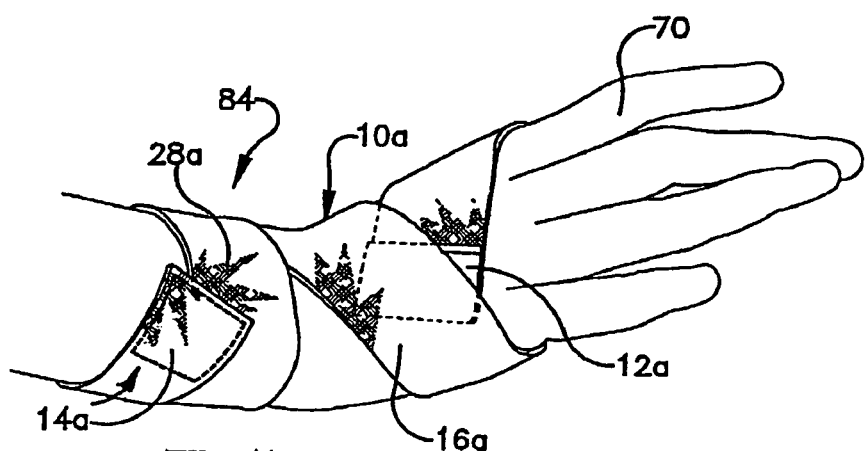

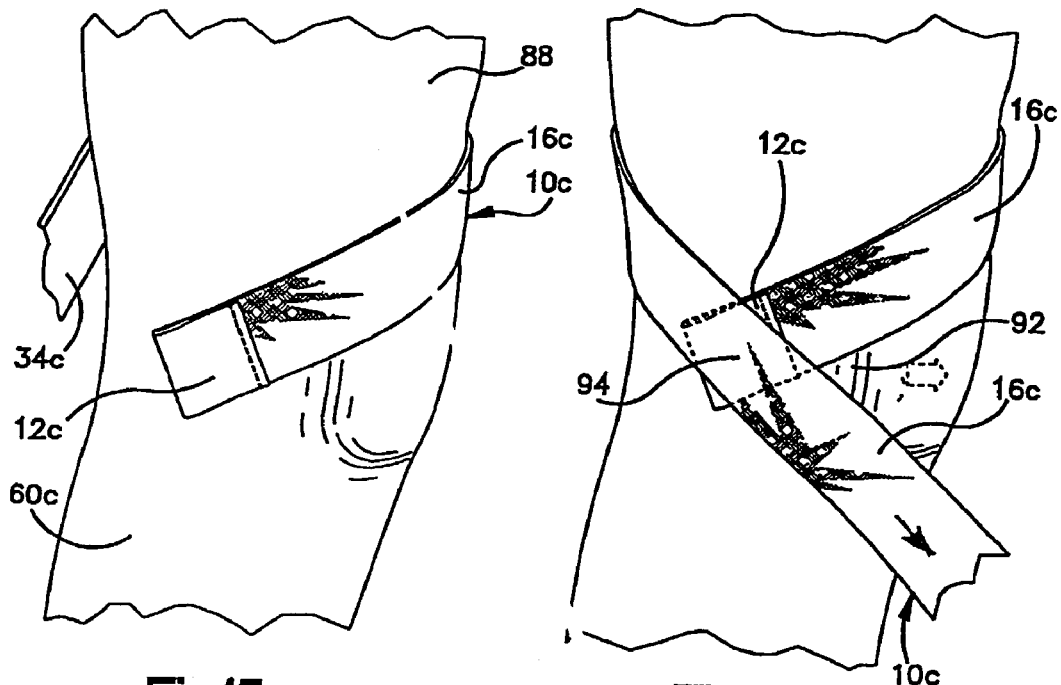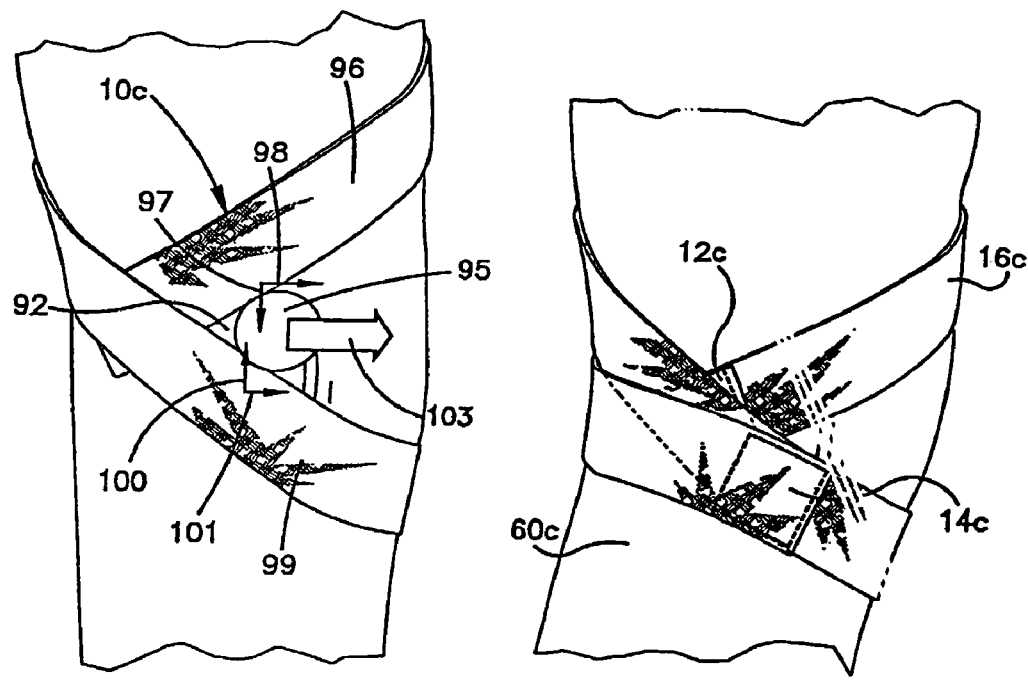

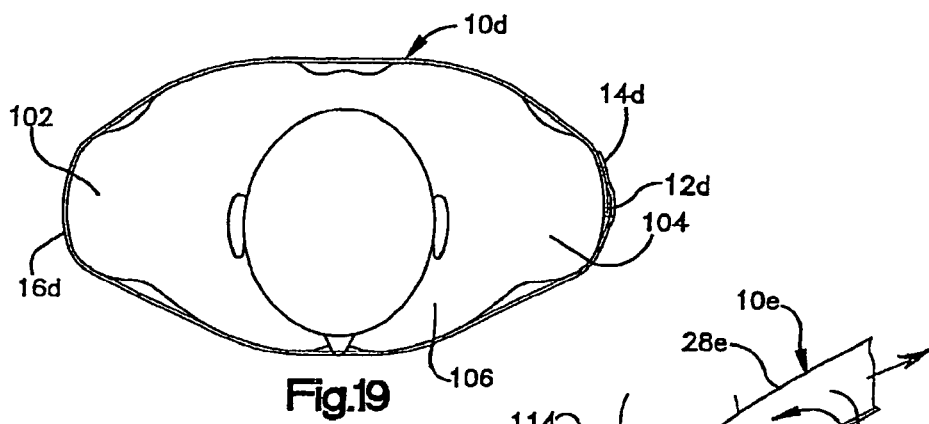
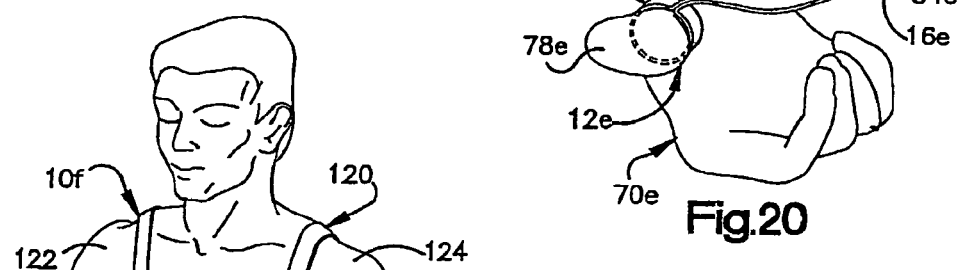
Fig.21
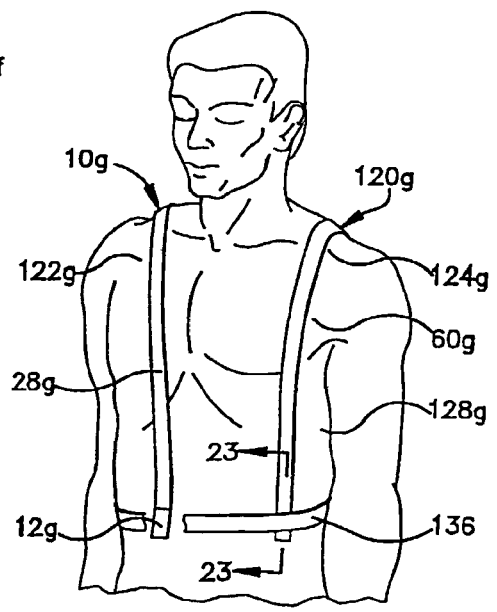
Fig.22

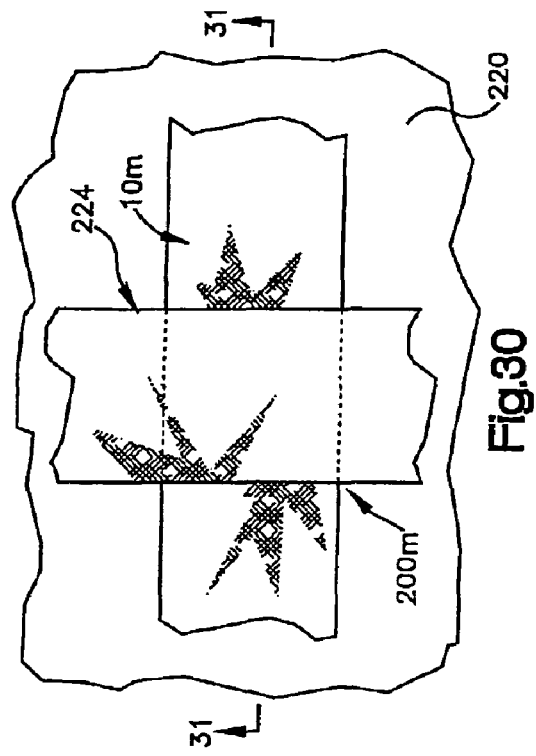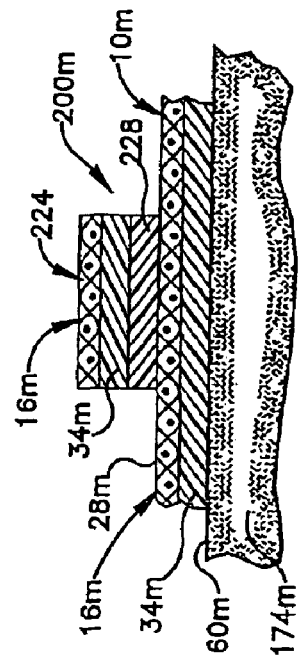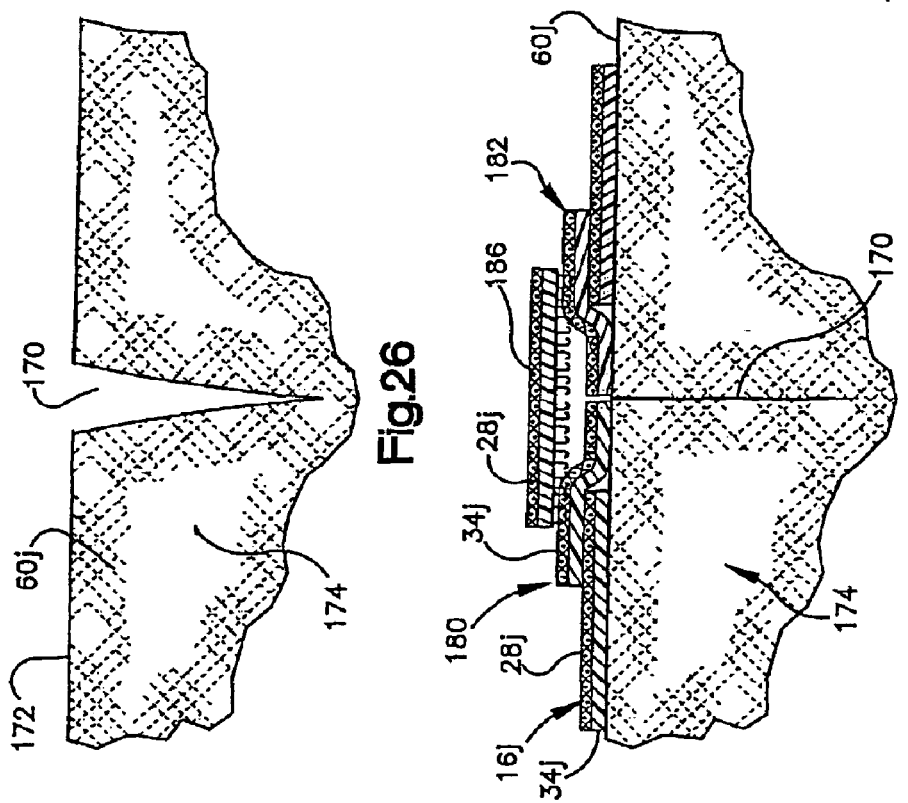

MYOFASCIAL STRAP

CROSS REFERENCE TO RELATED APPLICATIONS

This application is a continuation of patent application Ser. No. 10/439,418, filed May 16, 2003 now U.S. Pat. No. 6,958,048. Patent application Ser. No. 10/439,418 is a continuation of patent application Ser. No. 09/738,791, filed Dec. 15, 2000, now U.S. Pat. No. 6,575,926.

BACKGROUND OF THE INVENTION

The present invention relates to a new and improved strap and a method of using the strap to treat a patient.

A known strap for use in treating a patient includes a layer of foam which is connected with a layer of fabric. When the strap is to be utilized to treat a patient, the layer of foam is placed in engagement with the skin of the patient and the strap is wrapped around a portion of the patient. Known straps which may be utilized for treating a patient are disclosed in U.S. Pat. Nos. 2,811,154 and 5,036,838.

SUMMARY OF THE INVENTION

The present invention relates to a new and improved strap and method of using the strap for treatment of a patient. Base and second end portions of the strap may be interconnected by a main portion of the strap. The base end portion of the strap may have opposite sides with surfaces which are formed of foam. The main portion of the strap may have a first side with a surface which is formed of foam and a second side with a surface which is formed of fabric. If desired, the surfaces formed of foam could be formed of a different material. A retainer may be connected with the second end portion of the strap to connect the second end portion of the strap with the main portion of the strap.

When the strap is to be utilized to treat a patient, a layer formed of foam disposed on the first side of the strap may be placed in engagement with skin on the body of the patient. The base end portion of the strap is retained against movement relative to the body of the patient by wrapping the strap around a portion of the body of the patient and positioning a portion of the layer formed of foam on the first side of the strap in engagement with foam disposed on the second side of the base end portion of the strap. The second end portion of the strap may be connected with a fabric layer which forms the second side of the strap.

If desired, a plurality of straps may be utilized in the treatment of the patient. At least some of these straps may have a layer of foam disposed on a first side of the strap and a layer of fabric disposed on a second side of the strap. The layers of foam on the first sides of the straps may be positioned in engagement with the skin of the patient and the straps may be interconnected. Interconnecting of the straps may be performed by engaging foam on the second side, that is the fabric side, of a strap with the layer of foam on the first side of a strap. A retainer which, for example, may be a hook and loop type fastener, may be provided to connect an end portion of one strap with a layer of fabric on another strap or with a layer of fabric on the one strap.

It is contemplated that a strap constructed in accordance with the present invention may be utilized during the treatment of many different portions of a patient's body. For example, the strap may be utilized in conjunction with treatment of an arm, hand, leg, foot, shoulder, or other portion of a patient's body. A single strap may be wrapped around one or more portions of a patient's body. Alternatively, a first strap may be wrapped around one portion of a patient's body and a second strap may be connected with the first strap and wrapped around another portion of a patient's body.

The strap may be utilized to apply force to deep fascia, such as myofascial tissue. Of course, the strap may also be used to apply force to superficial fascia. It is contemplated that one or more of the straps may be used to increase a patient's proprioception. The straps may also be utilized to effect shifting of a bone, such as a patella, in the body of a patient. The straps may be used to connect one or more treatment devices with a patient.

BRIEF DESCRIPTION OF THE DRAWINGS

The foregoing and other features of the invention will become more apparent upon a consideration of the following description taken in connection with the accompanying drawings wherein:

FIG. 1 is a fragmentary top plan view of a strap constructed in accordance with the present invention;

FIG. 2 is fragmentary bottom plan view of the strap of FIG. 1;

FIG. 3 is an enlarged sectional view, taken generally along the line 3-3 of FIG. 1, illustrating the manner in which a layer of foam on one side of the strap and a layer of fabric on the opposite side of the strap are interconnected;

FIG. 4 is an enlarged fragmentary sectional view, taken generally along the line 4-4 of FIG. 1, and illustrating a retainer which is connected with one end portion of the strap;

FIG. 5 is an enlarged fragmentary sectional view, taken generally along the line 5-5 of FIG. 1, illustrating the manner in which foam is provided on opposite sides of a base end portion of the strap;

FIG. 6 is a fragmentary schematic illustration depicting the manner in which the strap of FIG. 1 is positioned relative to a portion of a patient's body with the base end portion of the strap in engagement with skin on the patient's body;

FIG. 7 is a fragmentary schematic illustration, generally similar to FIG. 6, illustrating the manner in which a portion of the strap is wrapped in a loop around a portion of the patient's body and engages the base end portion of the strap;

FIG. 8 is a fragmentary schematic illustration depicting the manner in which an end portion of the strap of FIGS. 6 and 7 is connected with fabric on one side of the strap;

FIG. 9 is a fragmentary schematic pictorial illustration depicting the manner in which the base end portion of the strap of FIG. 1 is positioned relative to a hand of a patient;

FIG. 10 is a fragmentary pictorial illustration depicting how a foam layer on one side of the strap of FIG. 9 is positioned in engagement with foam disposed on the base end portion of the strap to form a loop and to hold the base end portion of the strap against movement relative to the hand of the patient;

FIG. 11 is a fragmentary schematic pictorial illustration depicting the manner in which the strap is wrapped in a plurality of loops around a region where the hand and wrist of the patient are interconnected;

FIG. 15 is a schematic pictorial illustration depicting the manner in which the base end portion of the strap of FIG. 1 is positioned relative to a knee of a patient;

FIG. 16 is a fragmentary schematic pictorial illustration depicting the manner in which the strap is wrapped in a loop around the leg of the patient adjacent to the knee and engages the base end portion of the strap;

FIG. 17 is a schematic pictorial illustration depicting the manner in which loops of the strap of FIGS. 15 and 16 apply force to a patella in a knee of the patient;

FIG. 18 is a schematic pictorial illustration, generally similar to FIGS. 15 and 16, illustrating the manner in which the strap is further wrapped around the leg of the patient and in which an end portion of the strap is connected with fabric on one side of the strap;

FIG. 19 is a superior view of a patient illustrating the manner in which the strap of FIG. 1 is wrapped in a loop around the upper arms and trunk of the patient;

FIG. 20 is a fragmentary pictorial illustration depicting the manner in which a second embodiment of the strap of FIG. 1 is looped around the first finger (thumb) of a patient prior to wrapping of the strap in a plurality of loops around the hand and region where the hand and wrist of the patient are interconnected;

FIG. 21 is a fragmentary schematic pictorial illustration depicting the manner in which a pair of straps utilized in the treatment of scapula muscles and associated tissue in the body of a patient;

FIG. 22 is a schematic pictorial illustration depicting the manner in which a strap may be positioned around a trunk of the patient to retain straps for treatment of scapula muscles and associated tissue;

FIG. 26 is a fragmentary schematic illustration depicting an opening formed at a wound or incision in a patient's body;

FIG. 27 is a schematic fragmentary illustration depicting the manner in which the opening of FIG. 26 is closed by the use of a plurality of straps having the same construction as the strap of FIG. 1;

FIG. 28 (on sheet 2 of the drawings) is a schematic anterior view illustrating the manner in which the strap of FIG. 1 is connected with an upper portion of one arm and a shoulder of a patient;

FIG. 29 (on sheet 2 of the drawings) is a posterior view of the patient of FIG. 28 and illustrating the manner in which the strap extends between the arm and shoulder of the patient;

FIG. 30 (on sheet 9 of the drawings) is a schematic plan view illustrating the relationship of a plurality of straps to each other and skin on a portion of a patient's body;

FIG. 31 is a fragmentary sectional view, taken generally along the line 31-31 of FIG. 30, illustrating the manner in which the straps are interconnected.

DESCRIPTION OF SPECIFIC PREFERRED EMBODIMENTS OF THE INVENTION

Strap Construction

Figure 12:
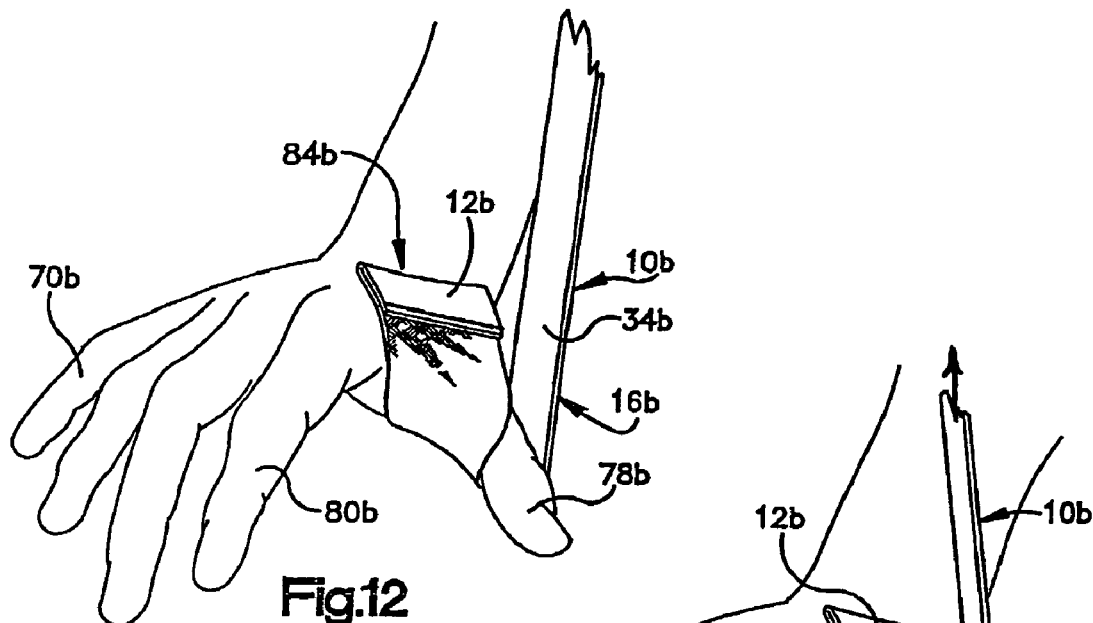
FIG. 12 is a fragmentary schematic pictorial illustration depicting the manner in which the base end portion of the strap of FIG. 1 is positioned relative to the hand and first finger (thumb) of a patient.

A strap 10 for use in treating a patient is illustrated in FIGS. 1 and 2. The strap 10 includes a base end portion 12, a second or retainer end portion 14, and a main portion 16. The main portion 16 extends between the base end portion 12 and retainer end portion 14. The strap 10 has an outer side 20 (FIG. 1) and an inner side 22 (FIG. 2). The inner and outer sides 20 and 22 extend between opposite ends of the strap 10.

The main portion 16 of the strap 10 has an outer side surface 26 (FIG. 1) formed by a layer 28 of fabric (FIG. 3). An opposite or inner side surface 32 (FIG. 2) of the strap 10 is formed by a layer 34 of foam. In the embodiment of the invention illustrated in FIG. 3, the layer 34 of foam is bonded directly to the layer 28 of fabric. It is contemplated that the layer 28 of fabric and layer 34 of foam may be interconnected in a manner similar to that disclosed in U.S. Pat. No. 5,036,838. In the illustrated embodiment of the invention, the layer 28 of fabric and the layer 34 of foam are coextensive with each other. Thus, the layer of fabric and the layer of foam both extend through the base end portion 12, main portion 16, and retainer end portion 14 of the strap 10.

The layer 28 of fabric (FIG. 3) is an elasticized polymeric material. The layer 28 of fabric has a loop-type weave similar to the material which forms the loop portion of a hook and loop fastener and is commercially available under the trademark "Velcro". The layer 28 of fabric has an outer side surface 26 which is relatively slippery. The surface 26 of the fabric layer 34 and the skin of a patient have a relatively low coefficient of static friction.

The loop weave of the elasticized fabric layer 28 enables it to be engaged by hook-type fasteners of the "Velcro" (trademark) type. Thus, the layer 28 of fabric has a loop pile which forms the outer side 20 of the strap 10. It is preferred to form the layer 28 of fabric with an elasticized construction so that the fabric can be stretched by pulling on the strap 10. However, if desired, the layer 28 of fabric could have a nonelasticized construction and could have a weave other than a loop weave.

The layer 34 (FIG. 3) of foam is connected directly to the layer 28 of fabric. The layer 34 of foam is formed with an open celled, elastomeric construction. The open celled elastomeric construction of the layer 34 of foam enables the layer to breath so that fluid can pass through the layer. The open celled construction of the layer of foam promotes patient comfort when the strap 10 is worn for a relatively long period of time.

The layer 34 of foam has a side surface 32 which has a relatively high adherence or grippiness compared to the surface 26 on the layer 28 of fabric. The surface 32 of the layer 34 of foam and the skin of a patient have a relatively large coefficient of static friction. The coefficient of static friction between the surface 32 and the layer 34 of foam and the skin of a patient is greater than the coefficient of static friction between the surface 26 of the layer of fabric 28 and the skin of a patient.

The layer 34 of foam is stretchable so that it can be stretched with the layer 28 of fabric. The elasticity of the layer 34 of foam is greater than the elasticity of the layer 28 of fabric. Thus, the modulus of elasticity of the layer 34 of foam is greater than the modulus of elasticity of the layer 28 of fabric.

The layer 34 of foam is an open celled foam of the urethane family and is stretchable in both the longitudinal and transverse directions to a greater extent than the layer 28 of fabric. This results in the layer 34 of open celled foam being supported by the layer 28 of fabric when the layer of fabric is in a stretched or non-stretched condition. It should be understood that the layer 34 of foam could be formed of any desired open celled or closed cell polymeric foam material. It is contemplated that the layer 34 could be formed of a polymeric material which is not a foam. The layer 34 could be formed of any material having a high coefficient of friction with skin.

One commercial source of material to form the strap 10 is Fabrifoam Products of Exton, Pennsylvania. Of course, other commercial sources of material for forming the strap 10 could be utilized if desired.

The layer 28 of fabric and the layer 34 of foam extend through the retainer end portion 14 of the strap 10 (FIGS. 2 and 4). A retainer 38 is provided at the retainer end portion 14 of the strap 10. The retainer 38 has a rectangular configuration (FIG. 2) and is fixedly connected with the layer 34 of foam and layer 28 of fabric by heat staking. Of course, the retainer 38 could be connected with the layer 34 of foam and the layer 28 of fabric by other methods if desired. For example, the retainer 38 could be bonded to the layer 34 of foam.

The retainer 38 has the same construction as the hook portion of a hook and loop fastener of the "Velcro" (trademark) type. Thus, the retainer 38 has an array of hooks 42 which are engagable with the loop-type fabric which forms the layer 28 of fabric. Although it is preferred to utilize a retainer 38 which is engagable with a layer 28 of fabric with a "Velcro" (trademark) hook and loop type fastening action, a different type of retainer could be utilized if desired. By forming the retainer 38 with the "Velcro" (trademark) hook type construction, the retainer 38 can be connected with the layer 28 of fabric at any location along the length of the layer of fabric. However, other types of retainers could be utilized if desired.

The base end portion 12 (FIG. 1) of the strap 10 is formed by doubling the layer 28 of fabric and the layer 34 of foam back on itself. This results in the base end portion 12 of the strap 10 having a double-layered construction illustrated in FIG. 5. Thus, the base end portion 12 has an upper (as viewed in FIG. 5) layer 48 and a lower layer 50 which are interconnected by a bend 52. The upper layer 48 is heat staked to the lower layer 50 to interconnect the upper and lower layers 48 and 50.

The overlapped construction of the base end portion 12 results in the layer 28 of fabric and the layer 34 of foam extending in a continuous manner from the main portion 16 of the strap 10 through the lower layer 50 of the base end portion 12, around the bend 52, and through the upper layer 48 of the base end portion 12. The layer 28 of fabric is integrally formed as one piece and extends throughout the entire extent of the strap 10. Similarly, the layer 34 of foam is integrally formed as one piece and extends throughout the entire extent of the strap 10.

It should be understood that the base end portion 12 could have a different construction. For example, the upper layer 48 could be formed by a separate rectangular segment formed of the same material of the main portion 16 of the strap 12. This separate rectangular segment of material may be heat staked to the lower layer 50 of the base end portion 12. Alternatively, the base end portion 12 could be formed with a single layer 28 of fabric with two separate layers of foam adhered to opposite sides of the single layer of fabric. Thus, a layer of foam could be adhered to the outer side surface 26 of the layer 28 of fabric throughout the extent of the base end portion 12 to provide a layer of foam which is separate from and on the opposite side of the strap from the layer 34 of foam.

Although a preferred construction for the strap 10 has been illustrated in FIGS. 1 through 5, it is contemplated that the strap 10 may have a different construction if desired. For example, rather than being formed by separate layers of foam and fabric, the strap 10 may be formed from a single layer of material. If desired, with such a construction, a separate base end portion 12 and retainer end portion 14 may be connected to the single layer of material. Alternatively, the strap 10 could be formed of multiple layers of fabric and/or multiple layers of foam. Although it is preferred to form the strap 10 with the layer 34 being an open celled urethane foam, the layer 34 could be formed of a substantially different material if desired.

The illustrated strap 10 has an outer side surface 26 which is slipperier than the inner side surface 32. This is because the outer side surface 26 is formed of a woven polymeric material while the inner side surface 32 is formed of a polymeric foam. It is contemplated that both the outer side surface 26 and the inner side surface 32 could be formed of one or more materials having substantially the same degree of roughness or gripping action.

In the illustrated embodiment of the strap 10, the only foam which is exposed on the outer side 20 of the strap 10 is on the base end portion 12 of the strap. It is contemplated that foam could be exposed at other locations on the outer side 20 of the strap 10. For example, a rectangular section of foam could be disposed on the outer side 20 of the strap 10 at a location midway between the base end portion 12 and the retainer end portion 14. This additional section of foam could be secured to the outer side 20 of the strap 10 by heat staking or by bonding directly to the outer side surface 26 of the layer 28 of fabric.

Use of Strap

The strap 10 of FIGS. 1-5 may be used in many different ways in association with many different portions of a patient's body. The strap 10 may be utilized to apply only compressive forces to tissue in the patient's body. Alternatively, the strap 10 may be used to provide a combination of compressive and tension forces in tissue in the patient's body. The combination of compressive and tension forces is particularly advantageous when it is desired to effect movement of superficial and/or deep fascia relative to other tissue in a patient's body. The combination of compressive and tension forces applied by a strap 10 can be utilized to effect shifting movement of one bone in a patient's body relative to another bone.

It is contemplated that the strap 10 may be utilized in many different types of patient treatments. It is believed that the strap 10 may be used during active, causal, expectant, palliative, preventive, supportive, and/or symptomatic treatments of a patient. For example, the strap 10 may be used to apply force to body tissue to alter the action of muscles and/or to change the relationship between adjacent body tissues at many different locations in a patient's body.

When the strap 10 is wound in a circular loop around a portion of a patient's body, the strap 10 may be utilized to provide a pure compressive force against tissue of the patient's body. However, when the strap 10 is wound in a spiral around a portion of the patient's body, the strap 10 exerts both compressive and tension forces against tissue of the patient's body. The magnitude of the compressive and tension forces may be varied by varying the tension in the strap 10. Thus, one turn of a spiral wrapping of the strap 10 around a portion of a patient's body may be formed with a first tension in the strap and a second turn of the spiral wrapping may be formed with a tension which is greater than the first tension to increase shear forces applied to body tissue.

When the strap 10 (FIG. 6) is to be wrapped around a patient's body in such a manner as to provide both tension and compressive forces on tissue of the patient's body, the strap 10 is oriented with the layer 34 of foam facing toward skin 60 on a portion 62 (FIG. 6) of the patient's body. The layer 28 of fabric faces outward away from the skin 60.

When the strap 10 is to be wrapped around the portion 62 of the patient's body, the base end portion 12 is positioned in engagement with the skin 60 of the patient. The upper layer 48 of the base end portion 12 faces away from the skin 60 (FIG. 6) on the portion 62 of the patient's body. Similarly, the lower layer 50 (FIG. 5) of the base end portion 12 is positioned in engagement with the skin 60 (FIG. 6) on the portion 62 of the patient's body. The inner surface 32 on the layer 34 of foam grips the skin 60 on the patient's body to retain the base end portion 12 against undesired movement relative to the patient's body. The base end portion 12 may be positioned in engagement with the patient's body by the patient or by medical personnel.

Regardless of whether the strap 10 is being positioned by the patient or another person, the base end portion 12 of the strap is manually pressed against the skin 60 to position the base end portion 12 of the strap relative to the portion 62 of the patient's body. The main portion 16 of the strap 10 is then wrapped in a loop around the patient's body, in the manner illustrated schematically in FIG. 6. As the main portion 16 of the strap 10 is wrapped in a loop around the patient's body, the layer 28 of fabric faces outward while the layer 34 of foam faces inward. This results in the layer 34 of foam being moved into engagement with the foam on the upper layer 48 of the base end section 12 (FIG. 7).

As the main portion 16 of the strap 10 moves into engagement with the base end portion 12 of the strap, the main portion 16 is tensioned and the base end portion 12 is pressed against the skin 60 of the patient. As the lower layer (FIG. 5) of the base end portion 12 is pressed against the skin 60 of the patient, the layer 34 of foam grips the skin 60 of the patient. As the layer 34 of foam on the main portion 16 of the strap 10 is pressed against the upper layer 48 of the base end portion, the layer 34 of foam on the main portion 16 of the strap 10 engages and firmly grips the layer 34 of foam on the upper layer 48 of the base end portion 12.

There is a relatively large coefficient of static friction between the inner side surface 32 (FIG. 3) of the layer 34 of foam on the main portion 16 of the strap 10 and the surface of the foam on the upper layer 48 (FIG. 5) of the base end portion 12 of the strap. This relatively large coefficient of static friction results in the main portion 16 of the strap 10 and the base end portion 12 of the strap being securely interconnected by a friction connection.

As the main portion 16 of the strap 10 is wrapped in loops around the portion 62 of the patient's body, the base end portion 12 of the strap 10 is pressed firmly against the skin of the patient. There is a relatively large coefficient of static friction between the inner side surface 32 on the layer 50 (FIG. 5) of the base end portion 12 and the skin 60 of the patient. This results in the base end portion 12 of the strap 10 being securely gripped between the portion 62 (FIG. 7) of the body of the patient and the main portion 16 of the strap 10. This results in the base end portion 12 being anchored against movement relative to the skin 60.

The friction connection established between the foam on the inside of the main portion 16 of the strap 10 and the foam on the outside of the base end portion 12 of the strap forms the first turn of the strap into a loop around the portion 62 of the patient. By tensioning the main portion 16 of the strap 10, the loop can be pulled toward the right, as viewed in FIG. 7. Pulling the loop around the portion 62 of the patient's body applies tension forces to the skin 62 of the patient. These tension forces are transmitted to body tissue beneath the skin of the patient. The rightward (as viewed in FIG. 7) tension forces apply shear stress to superficial fascia and to deep fascia in the body of the patient. The tension forces may be transmitted to fascia associated with muscles of the patient, that is myofascia.

As the main portion 16 of the strap 10 is wrapped across the base end portion 12 of the strap, the main portion of the strap is pulled toward the right (as viewed in FIG. 7). This results in the application of a combination of shear and compressive forces to the skin 60 and superficial fascia immediately beneath the skin 60. The application of shear forces to fatty tissue beneath the skin 60 can result in rupturing of fat globules and subsequent dissipation of the fat.

During a second turn or winding of the main portion 16 of the strap 10 around the portion 62 of the patient's body in a second loop, the strap continues to be pulled toward the right (as viewed in FIG. 7) with an increased force. Increased tension forces in the second loop have shear components extending along the axis about which the strap 10 is wound, that is, about the longitudinal central axis of the portion 62 of the patient's body. This results in the application of sidewise shear forces to deep fascia in the patient's body, such as myofascia. The sidewise shear forces applied to the deep fascia in the patient's body are effective to pull the deep fascia toward the right (as viewed in FIG. 7). As each successive turn of the strap 10 is wrapped around the portion 62 of the patient's body to form another loop, the force with which the strap is tensioned may be increased.

Increasing the tension forces in the strap 10 as the strap is wound around the portion 62 of the patient's body increases both the compressive force applied against the portion 62 of the patient's body and the shear forces applied to tissue beneath the skin 60 of the patient's body by the loops in the strap. The tension forces resulting from pulling the strap 10 have axial components. These axial components cause a shifting of the skin 60 of the patient toward the right (as viewed in FIGS. 7 and 8) and a shifting of both superficial fascia and deep fascia toward the right.

As the strap 10 is wrapped around the portion 62 of the patient's body, tension force, indicated by an arrow in FIG. 7, is transmitted from a loop being formed in the strap to previously formed loops in the strap. Thus, each of the loops formed in the strap 10, after the first loop, is effective to transmit force to an adjacent loop in the strap. The transmission of force between the loops of the strap has a compounding effect to increase the force transmitted to superficial fascia and deep fascia in the portion 62 of the patient as the strap 10 is wrapped around the portion 62 of the patient.

The extent of shifting movement of the deep fascia and/or other body tissue can be controlled by controlling the tension applied to the strap 10. Thus, the greater the shear or axially directed force which is to be applied to the deep fascia, the greater is the tension which is applied to the strap 10 as the strap is wound around the portion 62 of the patient's body. There is a relatively high coefficient of friction between the inner side surface 32 of the layer 34 of foam (FIG. 3) and the skin 60 (FIGS. 7 and 8) on the portion 62 of the patient's body. Therefore, substantial forces directed in an axial direction along the portion 60 of the patient's body can be applied by the strap 10 during winding and tensioning of the strap.

When the strap 10 has been fully wrapped in a series of loops around the portion 62 of the patient's body, the retainer end portion 14 of the strap is connected with the main portion 16 of the strap. To effect this interconnection, the retainer 38 (FIG. 4) on the retainer end portion 14 of the strap is pressed firmly against the layer 28 of fabric on the main portion 16 of the strap. As this occurs, the hooks 42 (FIG. 4) on the retainer 38 engage the loops of the layer 28 of fabric against which the retainer end portion 14 of the strap is pressed (FIG. 8). This results in the retainer end portion 14 of the strap 10 being connected to the main portion 16 of the strap to hold the strap against movement relative to the portion 62 of the patient's body.

Although only three turns of the strap 10 have been illustrated in FIG. 8 as being looped around the portion 62 of the patient's body, a greater or lesser number of could be wound around the patient's body. Of course, if additional turns of the strap 10 are to be wound around the portion 60 of the patient's body, the length of the strap 10 would be increased. Similarly, if fewer turns were to be wound around the portion 62 of the patient's body, the length of the strap would be decreased.

The strap 10 may be wrapped around a patient's forearm, in the manner illustrated in FIGS. 6-8, when the strap is being used in the treatment of tennis elbow or a similar disorder. Of course, the strap 10 may be wrapped around a patient's leg, in the manner illustrated in FIGS. 6-8, when the strap is being used in the treatment of a disorder associated with the patient's leg. Although the strap 10 is illustrated in FIGS. 6-8 as being wrapped around only one portion 62 of the patient's body, the strap could be wrapped around a plurality of portions of a patient's body if desired. This could be done in many different ways including a technique similar to the technique used in forming a buddy bandage between two portions of a patient's body.

In FIG. 8, the strap 10 is wound in a series of overlapping loops. However, it is contemplated that space could be provided between at least some of the loops. For example, after the first loop has been formed in the manner illustrated in FIG. 7, a next succeeding loop could be formed by winding the strap 10 around a portion of the patient's body which is spaced from the portion engaged by the first loop.

Figure 32:
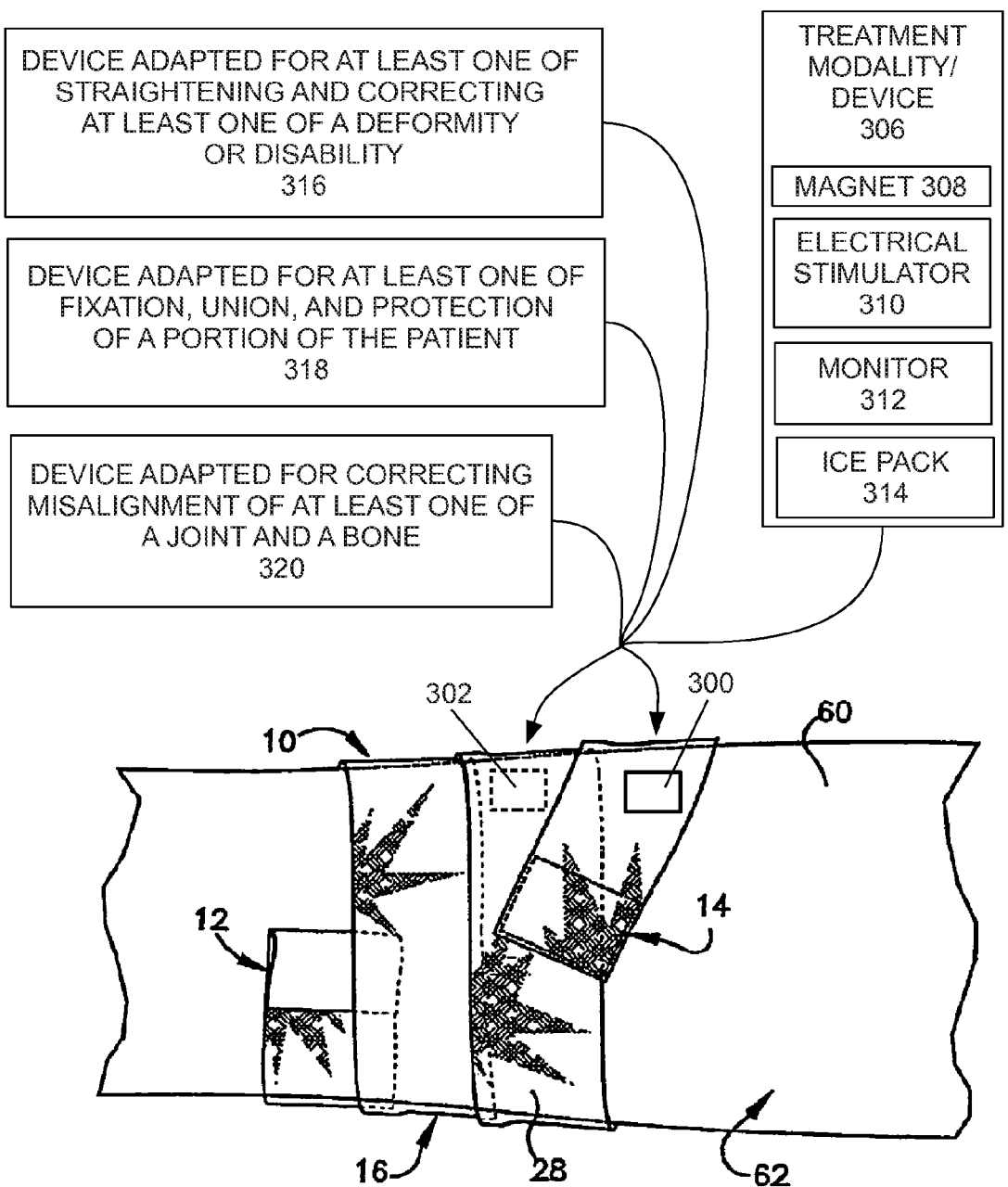
FIG. 32 is a fragmentary schematic illustration depicting example modalities/devices which may be held in position relative to the patient's body by the strap.

Referring to FIG. 32, it is contemplated that modalities/devices 306 could be held in position relative to a patient's body by the strap 10. For example, magnets 308 could be secured to the layer 28 of fabric by "Velcro" (trademark) hook type fasteners (at, for example, position 300) or could be positioned between the layer 34 of foam and the patient's body (at, for example, position 302). The strap 10 could be utilized to position electrical stimulus 310 or monitors 312 relative to the patient's body. If desired, the strap 10 could be used to position ice packs 314 relative to the patient's body.

It is contemplated that the device for use in treatment of portions of a patient's body may be held in place by the use of one or more straps having the same construction as the strap 10. These devices 316 may be utilized for many different purposes including the straightening or correction of a deformity or disability. A device 318 positioned by a strap having the same construction as the strap 10, may be used for the fixation, union or protection of a portion of a patient's body. The device 320 positioned by a strap 10 may be used to correct malalignment of joints, bones, or other portions of a patient's body. Although the strap 10 may be used to position many different devices 306, 316, 318, 320 relative to a patient's body, some devices which may be positioned by the strap 10 may have a construction similar to the construction of the devices illustrated in U.S. Pat. Nos. 433,227; 3,698,389; 4,441,489; 4,848,326; 5,685,830; and 5,848,979.

It is also contemplated that one or more straps, having the same construction as the strap 10, may be utilized to position a portion of a patient's body relative to a portion of a device spaced from a patient's body. For example, a strap having a construction similar to the construction of the strap 10 could be utilized to position a portion of a patient's body relative to an imaging apparatus, such as a magnetic resonance imaging unit (MRI). The strap 10 could be utilized in association with an apparatus similar to the apparatus disclosed in U.S. Pat. No. 5,577,503.

Use of Strap—FIGS. 9-11

In the embodiment of the invention illustrated in FIGS. 6-8, the strap 10 has been wound around a generally cylindrical portion of a patient's body, such as around a patient's forearm or the lower portion of a patient's leg. In the embodiment of the invention illustrated in FIGS. 9-11, the strap is wrapped around the patient's hand and the region of the patient's body where the patient's wrist and hand are interconnected. Since the embodiment of the invention illustrated in FIGS. 9 and 10 is generally similar to the embodiment of the invention illustrated in FIGS. 1-8, similar numerals will be utilized to identify similar components, the suffix letter "a" being added to the numerals of FIGS. 9 and 10 to avoid confusion.

When a strap 10*a* is to be wound around a hand 70 of a patient, a base end portion 12*a* (FIG. 9) of the strap 10*a* is positioned in engagement with the back 74 of the hand. The main portion 16*a* of the strap 10*a* is positioned between the first finger 78 (FIG. 10), that is, the thumb, and the second finger 80, that is, the forefinger. As the strap 10*a* is wrapped around the hand 70, the layer 34*a* of foam on the main section 16*a* of the strap engages the back 74 of the hand 70 and is positioned in engagement with the palm of the hand.

As the strap 10*a* is tensioned, the layer 34*a* of foam on the main portion 16*a* of the main portion of the strap is positioned in engagement with an exposed layer 6*f* foam on the base end portion 12*a* of the strap. There is a relatively large coefficient of static friction between the layer 34*a* of foam on the main portion 16*a* of the strap and the exposed layer of foam on the outer side of the base end portion 12*a* of the strap. There is also a large coefficient of static friction between the layer 34*a* of foam on the inner side of the base end portion 12*a* of the strap 10*a* and the skin on the hand 70 of the patient. These large coefficients of static friction result in the base end portion 12*a* of the strap being secured between the back 74 of the patient's hand 70 and the main portion 16*a* of the strap 10*a*.

As the strap 10*a* is wrapped in a loop around the patient's hand, in the manner indicated schematically by an arrow in FIG. 10, the strap is tensioned to firmly press the base end portion 12*a* of the strap 10*a* against the back 74 of the patient's hand 70. The strap 10*a* is pulled into engagement with the patient's wrist and is wrapped in a plurality of loops around a region 84 (FIG. 11) where the patient's hand, wrist, and forearm are interconnected. This force results in bones and/or other tissue in the patient's hand 70 being held in a desired relationship. In addition, shear forces are transmitted to myofascial tissue disposed adjacent to the strap 10*a*.

A retainer end portion 14*a* of the strap 10*a* is pressed against the layer 28*a* of fabric on the main portion 16*a* of the strap 10*a*. The retainer section 14*a* has a hook-type retainer, corresponding to the retainer 38 of FIG. 4, which securely anchors the retainer end portion 14*a* of the strap 10*a* against movement relative to the main portion 16*a* of the strap. By tensioning the strap 10*a* as it is wrapped around the region 84 where the hand, wrist, and forearm are interconnected in the wrist is held in extension.

The connection between the retainer section 14*a* and the loop in the strap 10*a* results in tension forces, indicated by an arrow in FIG. 11, being maintained. These tension forces are transmitted to myofascial tissue and bones in the hand, wrist and forearm of the patient.

In the embodiment of the invention illustrated in FIGS. 9-11, the base end portion 12*a* of the strap 10*a* has been positioned in engagement with the back 74 of the patient's hand 70. However, it is contemplated that the base end portion 12*a* of the strap could be located in a different position relative to the hand 70 if desired. For example, the base end portion 12*a* could be positioned in engagement with the palm of the hand 70.

Figure 13:
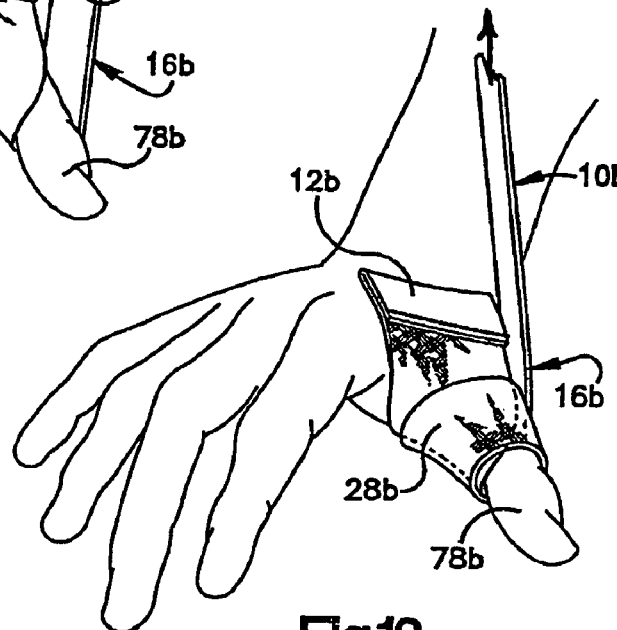
FIG. 13 is a schematic pictorial illustration depicting the manner in which the strap of FIG. 12 is wrapped in a plurality of loops around the first finger of the patient.
Figure 14:
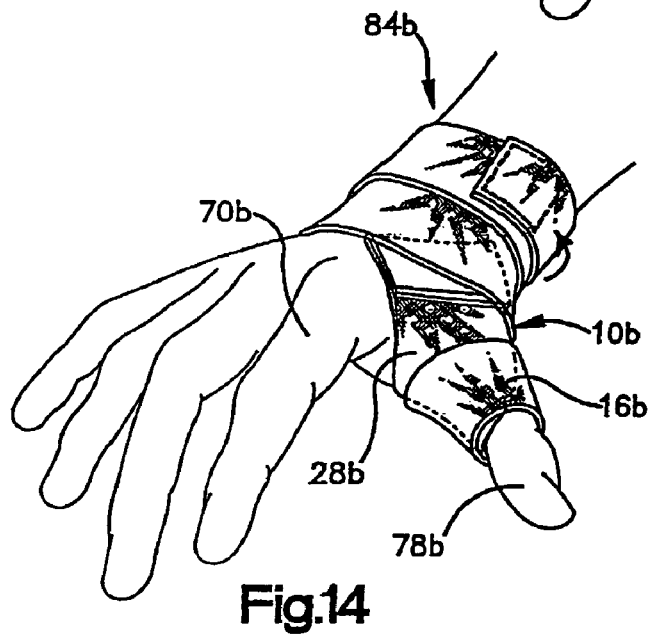
FIG. 14 is a schematic pictorial illustration depicting the manner in which the strap is wrapped in a plurality of loops around a region of the patient where a hand and wrist of the patient are interconnected.

Use of Strap—FIGS. 12-14

In the embodiment of the invention illustrated in FIGS. 9-11, the strap 10*a* is wrapped around the hand 70 and region 84 where the hand and wrist are interconnected. In the embodiment of the invention illustrated in FIGS. 12-14, the strap is wrapped around the first finger (thumb) and then wrapped around the region where the hand and wrist are interconnected. Since the embodiment of the invention illustrated in FIGS. 12-14 is generally similar to the embodiments of the invention illustrated in FIGS. 1-11, similar numerals will be utilized to designate similar components, the suffix letter "b" being added to the numerals of FIGS. 12-14 to avoid confusion.

A strap 10*b* is positioned relative to a patient's hand 70*b* (FIG. 12) with a base end portion 12*b* of the strap 10*b* disposed in a region 84*b* where the hand and wrist of the patient are interconnected. The layer 34*b* of foam on the inside of the base end portion 12*b* and main portion 16*b* of the strap 10*b* engages the skin on the hand 70*b* of the patient. Once the base end portion 12*b* of the strap 10*b* has been positioned against the back of the patient's hand, the strap 10*b* is pulled into the area between the first finger (thumb) 78*b* and second finger (fore finger) 80*b* on the hand of the patient (FIG. 12).

The main portion 16*b* of the strap 10*b* is then wrapped in a plurality of loops around the first finger (thumb) 78*b* (FIG. 13). As the first finger 78*b* is wrapped, the main portion 16*b* of the strap is tensioned and the layer 34*b* of foam is pressed firmly against the fabric layer 28*b* on the main portion of the strap 10*b*. Tension forces, indicated schematically by an arrow in FIG. 13, are transmitted to bones in the first finger 78*b* and to tissue connected with the first finger.

The strap 10*b* is then pulled downward and across the base end portion 12*b*. This results in the layer 34*b* of foam on the main portion 16*b* of the strap 10*b* being pressed against the exposed foam layer on the base end portion 12*b* of the strap (FIG. 14). There is a relatively large coefficient of static friction between the foam layer 34*b* on the main portion 16*b* of the strap 10*b* and the foam on the outside of the base end portion 12*b* of the strap 10*b*. There is also a relatively large coefficient of static friction between the foam layer 34*b* on the inside of the base end portion 12*b* and the skin on the back of the patient's hand 70*b*. This results in the base end portion 12*b* being securely held against movement relative to the hand 70*b* of the patient by engagement of the main portion 16*b* of the strap with the base end portion.

The strap 10*b* is then wrapped for a plurality of turns around the region 84*b* where the wrist, hand, and forearm of the patient are interconnected. A retainer end portion (not shown) having the same structure as the retainer end portion 14 of FIGS. 2 and 4 is then pressed against the fabric layer 28*b* on the main portion 16*b* of the strap 10*b* to anchor the retainer end portion. The retainer portion maintains tension force, indicated by an arrow in FIG. 14, in the strap 10*b*.

Although the strap 10*b* has been illustrated in FIGS. 12-14 as being wrapped around the first finger (thumb) 78*b* on the hand 70*b*, it is contemplated that the strap could be wrapped around a different finger if desired. Although the base end portion 12*b* of the strap 10*b* has been shown disposed adjacent to the back of the hand 70*b* of the patient, the base end portion 12*b* of the strap 10*b* could be positioned adjacent to the palm of the hand 70*b* if desired.

Use of Strap—FIGS. 15-17

In the embodiment of the invention illustrated in FIGS. 9-14, the strap is utilized in association with a hand of a patient. In the embodiment of the invention illustrated in FIGS. 15-17, the strap is utilized in association with a knee of the patient. Since the embodiment of the invention illustrated in FIGS. 15-17 is generally similar to the embodiments of the invention illustrated in FIGS. 1-14, similar numerals will be utilized to designate similar components, the suffix letter "c" being added to the numerals of FIGS. 15-17 to avoid confusion.

The patella or kneecap of a patient may tend to shift toward the outside of the knee of the patient. By applying force against the patella with a strap 10*c*, the patella can be moved medially inward from a laterally displaced position. It should be understood that the strap 10*c* could be utilized to move a patella back into alignment with a knee from a different position if desired. Thus, the strap 10*c* may be utilized to displace the patella back into a desired position. This may be accomplished by using the strap to pull the patella and deeper tissue—myofascial structures.

When the strap 10*c* is to be utilized to move a patella or kneecap on a right leg 88 of a patient from a laterally displaced position, a base end portion 12*c* of the strap 10*c* is positioned laterally or outward of the center of the right patella or kneecap (FIG. 15). The main portion 16*c* is pulled medially or inward across the top of the patella or kneecap in the manner illustrated schematically in FIG. 15.

As the strap 10*b* is wrapped around the right leg 88 of the patient, the layer 34*c* of foam on the main portion 16*c* of the strap 10*c* is positioned in engagement with skin 60*c* on a right leg of the patient. The main portion 16*c* of the strap 10*c* extends upward across the anterior side of the patient's leg 88 at a location immediately above the patella. When the strap reaches the center of the medial side of the leg, at a location above the patella, the strap is pulled laterally downward across the posterior side of the leg (FIGS. 15 and 16).

As the main portion 16*c* of the strap 10*c* is pulled downward across the outside of the knee in the manner illustrated in FIG. 16, the foam layer 34*c* on the strap engages the base end portion 12*c* of the strap to press the base end portion firmly against the skin 60*c* of the patient. The relatively large coefficient of static friction between the foam on the outside of the base end portion 12*c* of the strap 10*c* and the foam on the inside of the main portion 16*c* of the strap results in a secure connection between the base end portion and main portion of the strap. The relatively large coefficient of static friction between the foam on the inside of the base end portion 12*c* of the strap 10*c* and the skin on the leg of the patient results in a secure connection between the base end portion of the strap and the leg of the patient.

The resulting loop encircles the leg 88 of the patient immediately above the kneecap. As the strap 10*c* is pulled downward and leftward, as viewed in FIG. 16, force is applied to both the upper and lower portions of the kneecap (patella) by the strap. The resulting force component pushes the right kneecap inward toward the left kneecap.

The patella or kneecap is centered in a triangular space 92 formed by an intersection 94 (FIG. 16) between the main portion 16*c* of the strap 10*c* extending medially upward across an upper portion of the patella and a section of the main portion 16*c* of the strap 10*c* which extends medially downward and across a lower portion of the patella. These tension forces, indicated by an arrow in FIG. 16, are transmitted to body tissue disposed beneath the strap 10*c*. As the main portion 16*c* of the strap 10*c* is pulled downward and medially inward across the lower portion of the patella (FIG. 16), the main portion 16*c* of the strap is tensioned downward and forward relative to the knee of the patient. This results in the sections of the main portion 16*c* of the strap 10*c*, which form the triangular space 92, pressing against the patella to urge the patella medially inward from a laterally displaced position.

The manner in which force is applied against the patella by the strap 10c is illustrated schematically in FIG. 17 in association with a knee of a patient. The patella or knee cap is illustrated schematically in FIG. 17 and is designated by the numeral 95. It should be understood that FIG. 17 is a schematic frontal view of the patient's knee and the patella 95 has been illustrated in solid lines even though the patella is covered by skin and other body tissue.

The upper loop of the strap 10c has been designated by the numeral 96 in FIG. 17. The upper loop 96 of the strap 10c applies a downward force component 97 and a right ward (as viewed in FIG. 17) force component 98 to the patella 95. Similarly, the lower loop of the strap 10c has been designated by the numeral 99 in FIG. 17. The lower loop 99 of the strap 10c applies an upward force component 100 and a rightward (as viewed in FIG. 17) force component 101 to the patella 95.

The downward and upward force components 97 and 100 are substantially equal and cancel each other. The rightward force components 98 and 101 applied against the patella 95 result in a relatively large force 103 which moves the patella 95 toward the right (as viewed in FIG. 17). This results in body tissues around the patella 95 being tensioned under the influence of the force components 98 and 101 transmitted from the strap 10c.

The patella 95 is moved into alignment with the other bones in the leg 88 of the patient by the force applied against the patella by the strap 10c. The main portion 16c of the strap 10c is then pulled to the center of the inner side of the leg of the patient. The main portion 16c of the strap is then pulled upward and across the anterior portion of the leg 88 of the patient to form a pair of loops, that is, the upper loop 96 which extends around the leg and is disposed above the patella 95 and a lower loop which extends around the leg and is disposed below the patella. Force transmitted from the intersection 94 between the two loops formed by the main portion 16c of the strap 10c forces the patella toward the left on the leg of the patient and into alignment with the knee of the patient.

The retainer end portion 14c of the strap 16c is then connected with the main portion 16c of the strap at a location below the patella (FIG. 18). Rather than being connected with the downwardly extending section of the main portion 16c of the strap 10c, as shown in FIG. 18, the retainer end portion 14c could be connected with the section of the main portion 16c of the strap 10c which extends upward across the upper side of the patella.

Use of Strap—FIG. 19

In the embodiment of the invention illustrated in FIGS. 9-14 the strap is utilized in association with a patient's hand. In the embodiment of the invention illustrated in FIGS. 15-18 the strap is utilized in association with a patient's knee. In the embodiment of the invention illustrated in FIG. 19, the strap is utilized in association with the arms and shoulders of a patient. Since the embodiment of the invention illustrated in FIG. 19 is generally similar to the embodiment of the invention illustrated in FIGS. 1-18, similar numerals will be utilized to identify similar components, the suffix letter "d" being added to the numerals of FIG. 18 to avoid confusion.

A strap 10d has base end portion 12d, a main portion 16d and a retainer end portion 14d. The strap 10d is wrapped around the upper portion of right and left arms 102 and 104 and the trunk 106 of a patient. The strap 10d applies force against the upper portion of the arms 102 and 104. The strap 10d applies pressure against muscles and other body tissue connected with the shoulders of the patient. The strap 10d is effective to retard and increase proprioception of upward rotational movement of the arms 102 and 104.

When the strap 10d is to be positioned relative to the patient, the base end portion 12d of the strap is positioned against the upper portion of the left arm 104 (FIG. 19). The main portion 16d of the strap 10d is then tensioned across the back of the patient. The layer of foam on the main portion 16d of the strap, that is, the layer corresponding to the layer 34 of foam in FIG. 3, engages the skin on the back of the patient. The layer of fabric, that is the fabric layer corresponding to the layer 28 of FIG. 3, faces away from the skin of the patient.

While the base end portion 12d is held against movement, the main portion 16d of the strap 10d is tensioned and the strap positioned across the chest of the patient. The layer of foam on the main portion 16d of the strap is then moved into engagement with the upper layer of the base end portion 12d. The layer of foam on the section 16d of the strap engages the exposed foam on the base end portion 12d of the strap and is effective to anchor the base end portion 12d of the strap against movement. The retainer end portion 14d of the strap is then connected with the fabric layer on the main portion 16d of the strap.

Engagement of the layer of foam on the main portion 16d of the strap 10d with skin on the back and chest of the patient increases patient awareness of use of muscles and related tissue connected with the upper portions of the arms 102 and 104 of the patient. The increased patient proprioception facilitates treatment of upper arm and shoulder disorders. In addition, the strap 10d makes it easier for a patient to voluntarily limit the range of upper arm movement.

Use of Strap—FIG. 20

In the embodiment of the invention illustrated in FIGS. 1-19, the base end portion 12 of the strap 10 is positioned in engagement with skin on a portion of a patient's body and a layer of foam on the inside of the strap is positioned in engagement with foam on the outside of the base end portion. In the embodiment of the invention illustrated in FIG. 20, the base end portion of the strap is a preformed loop with foam on the inside. Since the embodiment of the invention illustrated in FIG. 20 is generally similar to the embodiments of the invention illustrated in FIGS. 1-19, similar numerals will be utilized to identify similar components, the suffix letter "e" being added to the numerals of FIG. 19 to avoid confusion.

A strap 10e is utilized in association with a hand 70e of a patient. The strap 10e has a base end portion 12e, a main portion 16e, and a retainer end portion (not shown) corresponding to the retainer end portion 14 of FIGS. 2 and 4. The main portion 16e of the strap 10e includes a layer 28e of fabric and a layer 34e of foam. The main portion 16e of the strap 10e has the same construction as the main portion 16 of the strap 10 of FIGS. 1-5. As was previously mentioned, the retainer end portion of the strap 10e has the same construction as the retainer end portion 14 of the strap 10 of FIGS. 1-5.

The strap 10e differs from the strap 10 of FIGS. 1-5 in that the base end portion 12e is a preformed loop 114 which is positioned around the first finger (thumb) 78e on the hand 70e of the patient. The inside of the loop 114 is completely lined by the layer 34e of foam. The outside of the loop 114 is formed by the layer 28e of fabric.

The loop 114 is formed by folding the end of the strap back on itself and heart staking the end of the strap to the main portion of the strap when a loop 114 of a desired diameter has been formed. This results in the inside of the loop being completely lined by the foam layer 34e. The outside of the loop is formed by the fabric layer 28e. The loop 114 is connected to the main portion 16e of the strap 10e where the loop is heat staked to the strap.

The size of the loop 114 will vary depending upon the finger on the hand 70 of the patient with which the loop is to be associated. Thus, if the loop is to be associated with the fifth finger (little finger) the loop would have a relatively small diameter. Similarly, if the strap 10e is to be utilized with a person having a relatively small hand, the loop 114 would be relatively small. However, if the loop 114 is to be associated with a relatively large muscular hand, the loop would be relatively large. It should be understood that it is contemplated that the strap 10e will be associated with any one of the fingers on hands of different sizes.

Once the loop 114 formed by the base end portion 12e of the strap 10e has been positioned around the first finger 78e on the hand 70e, the strap is wrapped around the first finger. As the main portion 16e of the strap 10e is wrapped around the first finger 78e, the foam layer 34e is pressed against the fabric layer 28e on the outside of the loop 114. The main portion 16e of the strap 10e is then wrapped around the region where the patient's hand and wrist are interconnected.

When the strap 10e is used, the loop 114 is placed around the first finger 78e. The main portion 16e of the strap 10e is tensioned and the strap is wrapped in a clockwise direction (as viewed in FIG. 20) around the first finger 78e. As this occurs, the layer 34e of foam on the main portion 16e of the strap 10e is pressed against the layer 28e of fabric on the outside of the loop 114.

After the strap 10e has been wrapped for more than one complete revolution about the first finger 78e, the strap is moved along the back of the thumb and across a portion of the back of the hand where the thumb is joined with the hand, to a region where the wrist and hand of the patient are interconnected. The strap is then wrapped for a plurality of turns in a clockwise direction about the wrist of the patient. The retainer end portion of the strap then engages the fabric layer 28e to secure the strap in the manner previously explained in conjunction with the embodiment of the strap illustrated in FIGS. 1-5.

In the embodiment of the invention illustrated in FIG. 20, the strap 10e is provided with a preformed loop 114 for engagement with a finger 78e on a hand 70e of a patient. However, it is contemplated that the loop could be preformed for engagement with another portion of a patient's body. For example, the size of the loop 114 could be increased so that the loop could be utilized to engage an upper portion of an arm of a patient. Alternatively, the loop could be sized so as to engage a portion of a leg of a patient. If desired, the loop 114 could be sized so as to engage a toe on a foot of a patient. Although only a single loop 114 has been illustrated in FIG. 20, a plurality of loops could be formed in the strap 10e if desired.

Use of Strap—FIG. 21

In the embodiment of the invention illustrated in FIGS. 1-5, the strap 10 is provided with a base end portion 12 and a retainer end portion 14. In the embodiment of the invention illustrated in FIG. 21, a plurality of straps which have the same construction throughout their length are utilized to apply force against shoulders of a patient. Since the embodiment of the invention illustrated in FIG. 20 is generally similar to the embodiments of the invention illustrated in FIGS. 1-20, similar numerals will be utilized to designate similar components, the suffix letter "f" being added to the numerals of FIG. 21 to avoid confusion.

The straps 10f and 120 are utilized to apply force against shoulders 122 and 124 of a patient. The straps 10f and 120 extend across the shoulders 122 and 124 of the patient and down posterior and anterior sides of a trunk 128 of the patient. Although the portions of the straps 10f and 120 disposed on the anterior side of the patient's trunk are illustrated in FIG. 21, it should be understood that the straps extend straight down the posterior side of the trunk 128 of the patient. Therefore, the portion of the straps which extend down the posterior side of the patient's trunk 128 extend generally parallel to and are aligned with the portions of the straps which extend down the anterior side of the patient's trunk. The straps 10f and/or 120 may be utilized in the treatment of a fractured clavicle or other bone in the shoulder of the patient.

The strap 10f has a uniform construction throughout its length. The strap 10f has the same construction as the main portion 16 of the strap 10 of FIGS. 1-3. Thus, the strap 10f includes an outer fabric layer 28f and an inner foam layer, corresponding to the foam layer 34 of FIG. 3. The inner foam layer of the strap 10f is disposed in engagement with skin on the trunk 128 of the patient.

Due to a gripping action between the foam layer on the inside of the strap 10f and the skin 60f on the trunk 128 of the patient, a tension force can be maintained in the strap 28f. This tension force is effective to apply pressure against scapula muscles to relieve myofascial pain or other maladies. In addition, the strap is effective to increase the patient's proprioception of the shoulder 122. Increased awareness of the shoulder 122 results from pulling of the strap 10f on the skin 60f of the trunk 128 of the patient during movement of the arm connected with the shoulder. Opposite ends of the strap 10f extend to the patient's waist. This enables opposite ends of the strap 10f to be held in position on the patient's trunk 128 by clothing, such as a belt, worn by the patient.

The strap 10f may be utilized by itself or in association with a second strap 120. The strap 120 has the same construction as the strap 10f and is positioned in the same manner relative to the opposite shoulder 124. The strap 120 cooperates with the patient's shoulder 124 and trunk 128 in the same manner as previously discussed in association with the strap 10f. It should be understood that either one of the two straps 10f or 120 may be utilized by itself without the other strap if desired.

Figure 23:
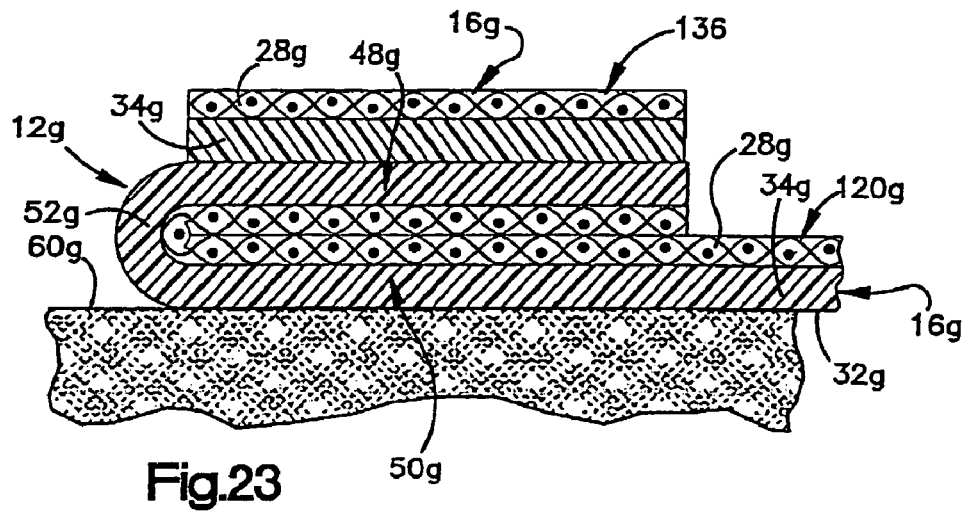
FIG. 23 is an enlarged fragmentary schematic illustration, taken generally along the line 23-23 of FIG. 22, illustrating one manner in which a plurality of straps may be interconnected.

Use of Strap—FIGS. 22 and 23

In the embodiment of the invention illustrated in FIG. 21, the two straps 10f and 120 are held in position relative to the trunk 128 of the patient by a gripping action between the layers of foam on the inside of the straps and the skin 60f of the patient along with clothing worn by the patient. In the embodiment of the invention illustrated in FIGS. 22 and 23, the straps over the shoulders of the patient are held in position relative to the trunk of the patient by a third strap which extends around the trunk of the patient. Since the embodiment of the invention illustrated in FIGS. 22 and 23 is generally similar to the embodiments of the invention illustrated in FIGS. 1-21, similar numerals will be utilized to designate similar components, the suffix letter "g" being added to the numerals of FIGS. 22 and 23 to avoid confusion.

Straps 10g and 120g extend across opposite shoulders 122g and 124g of a patient. The straps extend down posterior and anterior sides of a trunk 128g of the patient. The straps 10g and 120g apply force to scapula muscles and/or other tissue in the shoulders 122g and 124g of the patient. The straps 10g and/or 120g may be utilized in the treatment of a fractured clavicle or other bone in a shoulder of the patient.

The strap 10g is provided with base end portions at opposite ends of the strap. Thus, the strap 10g has a base end portion 12g at the end of the strap 10g disposed on the anterior side of the trunk 128g of the patient. Similarly, the strap 10g has a base end portion at the end of the strap on the posterior side of the trunk of the patient.

The base end portions at opposite ends of the strap 10g have the same construction as the base end portion 12 of FIGS. 1, 2 and 5. Thus, an anterior base end portion 12g of the strap 10g has a layer of foam, corresponding to the lower layer 50 of FIG. 5, which engages the skin 60g on the trunk of the patient. The end portion 12g of the strap 10g has an outer layer, corresponding to the upper layer 48 of FIG. 5, which faces outward away from the skin 60g on the anterior side of trunk 128g of the patient.

Although only the anterior side base end portion 12g of the strap 10g is illustrated in FIG. 22, it should be understood that there is a similar base end portion at the end of the strap 12g disposed on the posterior side of the trunk 10g of the patient. The two base end portions both have the same construction as the base end portion 12 of the strap 10 illustrated in FIGS. 1-5. The strap 10g does not have an end portion with a construction which corresponds to the construction of the retainer end portion 14 of the strap 10 of FIGS. 1-5.

The portion of the strap 10g extending between the opposite base end portions, that is, between the anterior base end portion 12g and the corresponding posterior base end portion, has the same construction as the main portion 16 of the strap 10 of the embodiment of the invention illustrated in FIGS. 1-5. Thus, the strap 10g has a layer of fabric 28g which extends for the entire length of the strap 10g. A layer of foam, corresponding to the layer 34 of foam of FIG. 3, is disposed on the side of the strap 10g toward the skin 60g of the patient. The layer of foam extends throughout the entire length of the strap 10g. The layer of foam on the inside of the strap 10g is effective to grip the skin 60g of the patient to hold the strap against movement relative to the skin.

The strap 120g has the same construction as the strap 10g. Thus, the strap 120g has a pair of base end portions with the same construction as the base end portion 12 of the strap 10 of FIGS. 1-5. There is a base end portion, with the same construction as the base end portion 12 of FIG. 5, at the end of the strap 120g disposed on the anterior side of the trunk 128g of the patient. Similarly, there is a base end portion with the same construction as the base end portion 12 of FIG. 5 at the end of the strap 120g disposed on the posterior side of the trunk of the patient. The posterior and anterior base end portions of the straps 10g and 120g are aligned with each other in a transverse plane extending through the trunk of the patient.

In accordance with a feature of the embodiment of the invention illustrated in FIG. 22, a retaining strap 136 extends around the trunk 128 of the patient. The retaining strap 136 holds the two straps 10g and 120g in desired positions relative to the trunk 128g and shoulders 122g and 124g of the patient. The retaining strap 136 has the same construction as the strap 10 of FIGS. 1-5.

The retaining strap 136 has a base end portion with foam on opposite sides of the base end portion, in the same manner as illustrated in FIG. 5. The retaining strap 136 has a retainer end portion with a retainer having the same construction as the retainer 38 of FIG. 4. The retainer end portion of the strap 136 has the same construction as the retainer end portion 14 of the strap 10 of FIG. 4. A main portion extends between the base end portion and retainer end portion of the retaining strap 136 of FIG. 22. The main portion of the retaining strap 136 has the same construction as the main portion 16 of the strap 10 of FIGS. 1-5.

When the straps 10g, 120g and 136 are to be utilized to treat a patient, the straps 10g and 120g are first positioned across the shoulders 122g and 124g and down the posterior and anterior sides of the trunk 128g. The retaining strap 136 is then positioned around the trunk 128g. The layer of foam on the main portion 16 of the retaining strap 136 engages the posterior and anterior base end portions of the strap 10g and the posterior and anterior base end portions of the strap 120g. Engagement of the layer of foam on the inside of the retaining strap 136 with the foam on the outside of the base end portions of the straps 10g and 120g holds the base end portions of the straps against movement relative to the trunk 128g of the patient.

When the retaining strap 136 is to be positioned around the trunk 128g of the patient, the base end portion of the retaining strap 136 is positioned on either the left or right side of the trunk adjacent to either the left or right arm of the patient. The main portion of the retaining strap 136 is then wrapped around the trunk of the patient. As this is done, the layer of foam, corresponding to the layer 34 of foam on the main portion 16 of the strap 10 (FIGS. 1-3), is positioned in engagement with the anterior and posterior base end portions 12g (FIG. 22) of the strap 10g. The layer of foam on the main portion of the retaining strap 136 is also positioned in engagement with the base end portions of the strap 120g disposed on the anterior and posterior sides of the trunk 128g of the patient.

The layer of foam on the inside of the main portion of the retaining strap 136 is then positioned in engagement with the layer of foam on the outside of the base end portion of the retaining strap 136. The retainer end portion of the retaining strap 136 is connected with the layer of fabric on the outside of the main portion of the retaining strap in the same manner as previously explained in conjunction with the embodiment of the invention illustrated in FIGS. 1-5.

In the embodiment of the invention illustrated in FIG. 22, the retaining strap 136 is positioned around the waist of the patient. However, it is contemplated that the retaining strap 136 could be positioned at a different location relative to the trunk 128g of the patient. For example, the retaining strap 136 could be positioned around the chest of the patient. If desired, a plurality of retaining straps, having the same construction as the retaining strap 136, could be positioned at a plurality of locations around the trunk 128g of the patient. Connector straps could be connected with and extend between the straps 10g and 120g on the posterior and/or anterior sides of the trunk of the patient. The relatively short connector straps could be used with or without the retaining strap 136.

The manner in which the retaining strap 136 cooperates with the strap 120g extending across the shoulder 124g (FIG. 22) of the patient is illustrated in FIG. 23. The shoulder strap 120g includes a main portion 16g having a layer 34g of foam and a layer 28g of fabric. The layer 34g of foam has an inner side surface 32g which engages the skin 60g of the patient.

The shoulder strap 120g has an anterior base end portion 12g (FIG. 23). The base end portion 12g of the strap 120g includes a lower or inner layer 50g and an upper or outer layer 48g. The layers 48g and 50g of the end portion 12g of the shoulder strap 120g are integrally formed as one piece with the main portion 16g of the shoulder strap. The layers 48g and 50g on the base end portion 12g of the shoulder strap 120g are fixedly connected to each other by heat staking. Of course, the layers 48g and 50g could be fixedly interconnected in a different manner if desired.

The retaining strap 136 has a main portion 16g which extends across the base end portion 12g of the shoulder strap 120g. The main portion 16g of the retaining strap 136 includes a layer 28g of fabric and a layer 34g of foam. The layer 34g of foam on the main portion 16g of the retaining strap 136 is disposed in engagement with the layer of foam on the upper or outer layer 48g of the base end portion 12g of the shoulder strap 120g. The gripping action between the layers of foam on the base end portion 12g of the shoulder strap 120g and the main portion 16g of the retaining strap 136 is effective to interconnect the two straps and hold them against movement relative to each other.

In the embodiment of the invention illustrated in FIGS. 22 and 23, the base end portion 12g of the shoulder strap 120g (FIG. 22) includes an upper or outer layer 48g and a lower or inner layer 50g having layers of fabric and foam which are integrally formed as one piece with the layer 28g of fabric and the layer 32g of foam of the main portion 16g of the strap 120g. However, a layer of foam could be bonded directly on the outer or upper side of the layer of fabric 28g which extends through the lower layer 50g of the base end portion 12g of the shoulder strap 120g. This would result in the base end portion 12g of the shoulder strap having only a single layer of fabric rather than the two layers formed by doubling over the layer 28g of fabric.

In the embodiment of the strap 120g illustrated in FIGS. 22 and 23, the shoulder strap 120g ends at the retaining strap 136. However, if desired, the shoulder strap 120g could extend downward past the retaining strap 136. If this was done, the shoulder strap 120g would extend to the left (as viewed in FIG. 23) of the retaining strap 136. With such a construction, it is believed that it may be preferred to bonded a layer of foam directly on the layer 28g of fabric of the shoulder strap 120g for engagement by the retaining strap 136. Alternatively, a separate piece or segment of the strap material could be connected to the main portion 16g of the shoulder strap 120g by heat staking. This would result in a construction similar to that illustrated in FIG. 23 with the exception of elimination of the bend 52g between the upper or outer layer 48g and the lower or inner layer 50g and in continuation of the main portion 16g of the strap 120g to the left (as viewed in FIG. 23) of the retaining strap 136.

Although two shoulder straps 10g and 120g have been illustrated in FIG. 22, a single shoulder strap could be utilized if desired. It should be understood that a plurality of retaining straps 136 could be used with one or more shoulder straps if desired. When two shoulder straps 10g and 120g are utilized, short connector straps may be extended between the shoulder straps. Although it is believed that the retaining strap 136 will be used with the connector straps, the connector straps may be used without the retaining straps.

Figure 24:
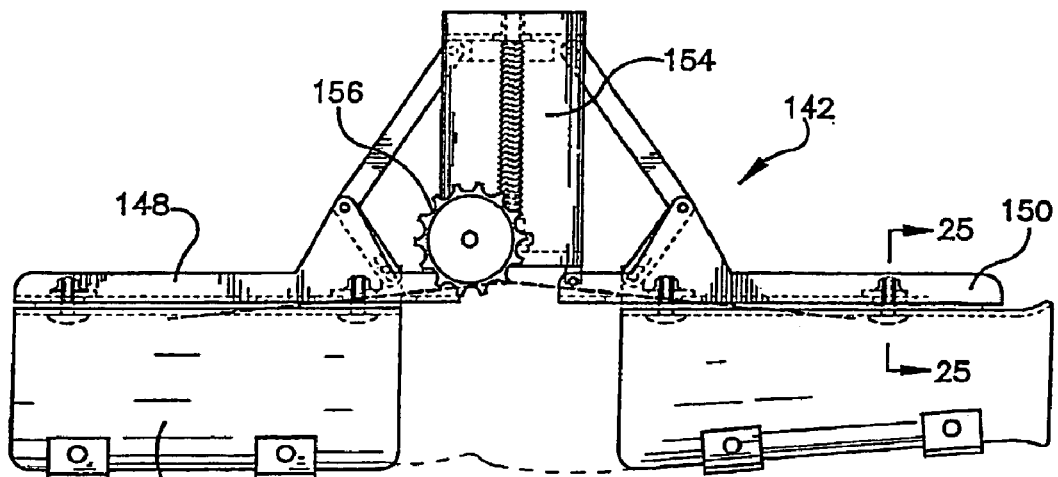
FIG. 24 is a schematic illustration of an orthosis which may be connected with portions of a patient's body.
Figure 25:
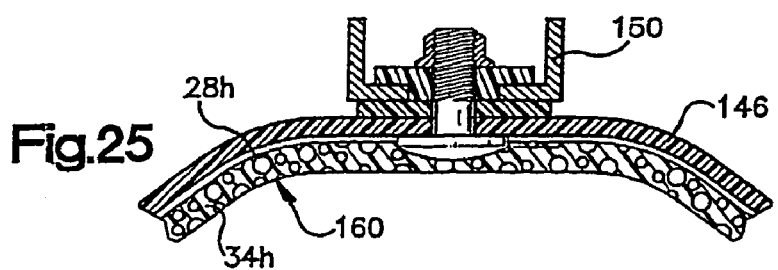
FIG. 25 is a schematic sectional view, taken generally along the line 25-25 of FIG. 24, illustrating the manner in which a cuff of the orthosis of FIG. 24 is lined.

Use of Strap Material—FIGS. 24 and 25

In the embodiments of the invention illustrated in FIGS. 1-23, the layers of foam and fabric have been used as strap material. In the embodiment of the invention illustrated in FIGS. 24 and 25, the layers of foam and fabric are utilized as a lining for an orthosis. Since components of the embodiment of the invention illustrated in FIGS. 24 and 25 are similar to components of the invention illustrated in FIGS. 1-23, similar numerals will be utilized to designate similar components, the suffix letter "h" being associated with FIGS. 24 and 25.

An orthosis 142 is illustrated in FIG. 24. The orthosis 142 is illustrated schematically in association with an arm of a patient to move an elbow joint disposed between the upper arm and forearm of the patient. However, it should be understood that the orthosis 142 could be utilized in association with other portions of a body of a patient. It is contemplated that the orthosis 142 will be utilized to effect a static progressive stretching of viscoelastic tissue associated with a joint in a body of a patient.

The orthosis 142 includes a cuff 144 which is attachable with an upper portion of an arm of a patient and a cuff 146 which is attachable with a lower portion of an arm of a patient. The cuff 144 is slidable along a cuff arm 148. Similarly, the cuff 146 is slidable along a cuff arm 150.

A tower 154 is connected with the cuff arms 148 and 150. A drive mechanism 156 is connected with the tower 154 and the cuff arms 148 and 150. The drive mechanism 156 is manually operated. However, a motor could be utilized to operate the drive mechanism 156 if desired.

During use of the orthosis 142, the drive mechanism 156 is operated to cause the cuff arms 148 and 150 to pivot about connections with the tower 154. As the cuff arms are pivoted relative to the tower 154, the cuffs 144 and 146 move along the cuff arms.

The construction and manner of use of the orthosis 142 is the same as is disclosed in U.S. Pat. No. 5,453,075. The disclosure in the aforementioned U.S. Pat. No. 5,453,075 is hereby incorporated herein in its entirety by this reference thereto. The orthosis could have a different construction than the specific construction of the orthosis 142. For example, the orthosis could have a construction similar to that disclosed in U.S. Pat. Nos. 5,685,830 or 5,848,979.

In accordance with a feature of the invention, the cuffs 144 and 146 of the orthosis are lined with the same material which forms the main portion 16 of the strap 10. Thus, the cuff 146 has a lining 160. The lining 160 includes a layer 28h of fabric which is fixedly secured, for example, by adhesive and/or heat staking, to the cuff 146. A layer 34h of foam is provided on the inside of the lining 160. The layer 34h of foam engages the skin on the patient's body. It should be understood that the layer 28h of fabric and the layer 34h of foam has the same construction as the layer 28 of fabric and the layer 34 of foam of FIGS. 1-5.

Use of Straps—FIGS. 26 and 27

In the embodiment of the invention illustrated in FIGS. 25 and 26, a plurality of straps are utilized to close an opening in a patient's skin. Since the straps of the embodiment of the invention illustrated in FIGS. 26 and 27 have the same general construction as the straps of the embodiment of the invention illustrated in FIGS. 1-23, similar numerals will be utilized to designate similar components, the suffix letter "j" being associated with the numerals of FIGS. 26 and 27 to avoid confusion.

An opening 170 (FIG. 26) is formed in the body of a patient. The opening extends through an outer surface 172 of the skin 60j of the patient into body tissue 174 disposed beneath the skin. The opening 170 may be formed by an incision, wound, or other cause.

In order to promote healing of body tissue, it is desirable to close the opening and press the body tissue 174 on opposite sides of the opening firmly together. This is accomplished by utilizing a pair of straps 180 and 182 (FIG. 27). The straps 180 and 182 are wrapped around a portion of the patient's body in which the opening 170 is disposed. The straps 180 and 182 are disposed on opposite sides of the opening 170.

The straps 180 and 182 apply tension forces to the body tissue 174 urging the body tissue on one side of the opening toward the body tissue on the other side of the opening. These tension forces are effective to close the opening 170 in the manner illustrated schematically in FIG. 27. An optional connector member 186 extends between the straps 180 and 182 and cooperates with the straps to hold the opening 170 closed. If desired, the connector member 186 could be eliminated and the opening 170 held in the closed condition of FIG. 27 by only shear or tension forces applied to the body tissue 174 by the straps 180 and 182.

The straps 180 and 182 have the same construction as the strap 10 of FIGS. 1-5. Thus, the strap 180 has a base end portion corresponding to the base end portion 12 of the strap 10, a main portion corresponding to the main portion 16 of the strap 10, and a retainer end portion corresponding to the retainer end portion 14 of the strap 10. Similarly, the strap 182 has a base end portion corresponding to the base end portion end portion 12 of the strap 10, a main portion corresponding to the main portion 16 of the strap 10 and a retainer end portion corresponding to the retainer end portion 14 of the strap 10. The two straps 180 and 182 both have the same construction as the strap 10 and are positioned around a portion of a patient's body in the same manner as previously described in conjunction with the strap 10.

A layer 34j of foam on a main portion 16j of the strap 180 is disposed in engagement with the skin 60j on one side, that is the left side as viewed in FIG. 27 of the opening 120. A second turn of the main portion 16j of the strap overlies a portion of the first turn of the strap. The layer of foam in the main portion of the second turn of the strap 34j engages a layer 28j of fabric in the first turn of the strap. The second loop of the strap 180 is tensioned and pulled toward the right (as viewed in FIG. 27) to apply force to the skin 60j.

The force applied to the skin 60j has a radially inward or compressive component and a tension component which extends parallel to the surface of the skin 60j. The tension component of the force applied to the skin 60j by the second turn of the strap 180 pulls the skin and underlying body tissue 174 toward the right (as viewed in FIG. 27). This rightward movement of the body tissue 174 results in a partial closing of the opening 170.

The strap 182 has the same construction as the strap 180. However, the second turn or winding of the strap 182 applies a leftward (as viewed in FIG. 27) force component to the skin 60j and body tissue 174. This leftward force component moves the skin 60j and body tissue on the right side of the opening 174 toward the skin and body tissue on the opposite or left side of the opening. This results in the opening being closed in the manner illustrated schematically in FIG. 27.

When the opening 170 is closed by oppositely directed shear or tension forces applied to the body tissue 174 by the straps 180 and 182, the body tissue on opposite sides of the opening is pressed together. Pressing the body tissue 174 on opposite sides of the opening 170 together promotes healing of the body tissue and permanent closing of the opening 170.

Although the straps 180 and 182 have been wrapped around the patient's body for only two complete turns, it is contemplated that the straps could be wrapped around the body tissue for additional turns if desired. If this was done, the tension or shear forces applied to the body tissue 174 tending to close the opening 170 would be increased. Of course, the wrapping of the straps 180 and 182 around the portion of the patient's body in which the opening 170 is formed would begin at a location spaced further from the opening to accommodate the additional turns of the straps.

An optional connector member 186 is illustrated in FIG. 27 as extending between the straps 180 and 182. The connector member 186 has the same construction as the retainer 38 of FIG. 4. Thus, the connector member 186 has a plurality of hooks which are engagable with the loop fabric layers 34j on the outside of the straps 180 and 182.

The connector member 186 can be utilized to apply forces to the straps 180 and 182 urging them toward each other in order to further promote closing of the opening 170. Alternatively, the connector member 186 may merely be pressed in place against the straps 180 and 182 after the opening 170 has been closed by the shear forces applied to the body tissue 174 by the straps 180 and 182. This would result in the connector member 186 being effective to prevent separation of the straps 180 and 182 and subsequent reformation of the opening 170 after the opening has been closed.

When the opening 170 is disposed on a portion of a patient's body which is subjected to forces tending to re-establish the opening 170 during normal daily activities of the patient, it is believed that the connector member 186 will be particularly advantageous. Of course, in certain situations at least, the connector member 186 may be eliminated.

Use of Strap—FIGS. 28 and 29

In the embodiment of the invention illustrated in FIGS. 28 and 29, the strap is utilized to restrain movement of an arm of the patient. Since the embodiment of the invention illustrated in FIGS. 28 and 29 is generally similar to the embodiments of the invention illustrated in FIGS. 1-23, similar numerals will be utilized to designate similar components, the suffix letter "k" being added to the numerals of FIGS. 28 and 29 to avoid confusion.

A strap 10k is wrapped around an arm 102k and extends horizontally across posterior side of a trunk 128k of a patient in the manner illustrated schematically in FIG. 29. The strap 10k extends beneath the axilla between an arm 104k and the trunk 128k of the patient. The strap extends upward across the anterior side of the trunk 128k of the patient adjacent to the arm 104k. The strap 10k extends across the shoulder 124k of the patient (FIGS. 28 and 29). The strap 10k extends downward across the posterior side of the shoulder 124k and trunk 128k of the patient (FIG. 29) to a connection 200 with a portion of the strap 10k extending across the posterior side of the trunk 128k of the patient.

Tension in the strap 10k urges the arm 102k of the patient toward the trunk 128k of the patient and in a posterior direction. The strap 10k tends to limit abduction of the right arm 102k of the patient. Of course, if the strap 10k was wrapped around the upper portion of the left arm 104k of the patient and extended across the right shoulder 122k of the patient, abduction of the left arm 104k would be limited. The strap 10k may be utilized in the treatment of a fractured clavicle or other bone in the shoulder of the patient.

When the strap 10k is connected with the right arm 102k and extends across the left shoulder 124k of the patient, in the manner illustrated in FIGS. 28 and 29, proprioception of the patient to movement of the right arm 102k is increased. This is because the layer of foam on the portion of the strap 10k extending across the posterior side of the trunk 128k and extending downward across the posterior side of the left shoulder 124k of the patient transmits force to the skin 60k on the posterior side of the trunk 128k of the patient. This force increases the patient's awareness of how the right arm 102k is being moved.

The strap 10k has the same construction as the strap 10 of FIGS. 1-5. Thus, the strap 10k (FIGS. 28 and 29) has a base end portion, corresponding to the base end portion 12 of the strap 10, a main portion 16k corresponding to the main portion of the strap 10 and a retainer end portion 14k corresponding to the retainer end portion 14 of the strap 10. The retainer end portion 14k of the strap 10k is connected with the main portion 16k of the strap 10k at the intersection 200 (FIG. 29) between the portion of the strap 10k which extends across the posterior side of the trunk of the patient in a transverse plane and the portion of the strap 10k which extends downward from the shoulder 124k across the posterior side of the trunk 128k.

When the strap 10k is to be connected with the patient in the manner illustrated in FIGS. 28 and 29, the base end portion of the strap 10k, corresponding to the base end portion 12 of the strap 10, is positioned in engagement with the front side of the upper arm of the patient at a location indicated by the numeral 204 in FIG. 28. The layer of foam on the inside of the main portion 16k is positioned in engagement with the skin on the upper portion of the right arm of the patient. The strap 10k is then wrapped across the portion of the upper arm of the patient which is furthest from the trunk of the patient. The strap 10k is then is wrapped across the portion of the upper arm at the axilla between the right arm 102k and the trunk 128k of the patient.

The main portion 16k of the strap 10k is then pulled across the base end portion of the strap 10k at the location designated by the numeral 204 in FIG. 28. This results in the foam layer on the inside of the strap, that is the foam layer corresponding to the foam layer 34 of FIGS. 1-5, engaging foam on the base end portion of the strap. The strap 10k is then wrapped, for a second time, across the upper portion of the right arm 102k which is furthest from the trunk 128k of the patient. This results in the formation of a loop around the upper portion of the right arm 102k of the patient.

The strap is then pulled across the posterior side of the patient's trunk. The tension in the main portion 16k of the strap 10k firmly presses the base end portion of the strap 10k against the skin of the patient. The tension force and engagement of the layer of foam on the main portion 16k of the strap 10k with the layer of foam on the outside of the base end portion of the strap 10k holds the main portion 16k of the strap against movement relative to the loop which extends around the upper portion of the right arm 102k of the patient.

The tension in the main portion 16k of the strap results in the layer of foam on the inside of the main portion of the strap 16k being pressed firmly against the posterior side of the trunk 128k of the patient. The strap 16k is then moved through the axilla formed between the upper portion of the left arm 104k and trunk 128k of the patient. The strap 10k is then pulled upward across the left shoulder 124k (FIG. 28) and then downward and rightward across the posterior side of the trunk 128k of the patient (FIG. 29). The retainer end portion 14k of the strap 10k is then pressed firmly against the layer of fabric on the outside of the main portion 16k of the strap 10k to form a loop which extends around the left shoulder 124k and a portion of the trunk 128k of the patient.

When the strap 10k is pulled downward, in the manner indicated by the arrow in FIG. 29, force is transmitted to body tissue disposed beneath the strap. This tension force may be utilized to urge one or more bones in the shoulder 124k of the patient into a desired relationship. The tension force is also transmitted through the layer of foam on the inside of the strap 16k to superficial fascia and deep fascia which are disposed in the patient's body near the strap.

If desired, a second strap may be connected with the strap 10k. The second strap may be provided with two retainer end portions, corresponding to the retainer end portion 14 of FIGS. 2 and 4 and no base end portion, corresponding to the base end portion 12. One of the retainer end portions of the second strap may be connected to the anterior portion of the loop around the right arm 102k of the patient and extend across the right shoulder 122k of the patient to the main portion 16k of the strap 10k which extends across the trunk 128k of the patient in a transverse plane. Of course, the second strap could be connected with the first strap 10k in a different manner if desired.

In the embodiment of the invention illustrated in FIGS. 28 and 29, a single strap 10k is utilized. However, a plurality of straps could be utilized if desired. One of the straps could be wrapped around the upper portion of the right arm 102k of the patient and the other strap could be wrapped around the upper portion of the left arm 104k of the patient. The two straps could be interconnected at a central portion of the trunk 128k of the patient. The use of the straps may be particularly advantageous when treating a fractured clavicle or other bone in either or both of the shoulders of the patient.

If desired, a single, relatively long strap could be provided to form loops around both shoulders 122k and 124k of the patient. Each loop of the two loops would extend around one of the shoulders of the patient in the same manner as in which the strap 10k extends around the left shoulder 124k of the patient in FIGS. 28 and 29. The base end portion of the strap may be positioned at any desired location on the patient, for example, on top of the right shoulder 122k. The single long strap would then be wrapped around the right shoulder 122k for one or more turns and around the left shoulder 124k for one or more turns. The retainer end portion may then be connected with the layer of fabric on the main portion of the strap.

The strap 10k which extends around one shoulder 124k, a plurality of straps which extend around both shoulders 122k and 124k, or a single long strap which extends around both shoulders may be utilized to position modality and/or a monitor relative to the body to the patient. The modality may include a magnet, electrical stimulator, monitor or ice pack. The use of the strap 10k or a plurality of straps may be advantageous in holding a monitor, such as a heart monitor, relative to the body of the patient.

Use of Strap—FIGS. 30 and 31

In the embodiment of the invention illustrated in FIGS. 1-5, the only foam which is exposed on the outer side 20 (FIG. 1) of the strap is the foam on the base end portion 12 of the strap. The layer 28 of fabric extends across the outer side 20 of the main portion 16 and retainer portion 14 of the strap 10. In the embodiment of the invention illustrated in FIGS. 30 and 31, foam is exposed at two locations on the outer side of the strap, that is, at the base end portion and at a location on the main portion of the strap. Since the embodiment of the invention illustrated in FIGS. 30 and 31 is generally similar to the embodiments of the invention illustrated in FIGS. 1-23, similar numerals will be utilized to designate similar components, the suffix letter "m" being added to the numerals of FIGS. 30 and 31 to avoid confusion.

A strap 10m is wrapped around a portion 220 of the patient's body. A second strap 224 is connected with the first strap 10m at an intersection 200m. The two straps may extend around any desired portion of a patient's body.

In accordance with a feature of this embodiment of the invention, a foam section 228 (FIG. 31) is provided at the intersection 220 to interconnect the straps 10m and 224. The section 228 of foam is fixedly secured to the layer 28m of fabric of the strap 10m at a main portion 16m of the strap 10m. A layer 34m of foam on a main section 16m of the strap 224 engages the section 228 of foam. The relatively high coefficient of friction between the surfaces of the layer 34m of foam on the strap 224 and the section 228 of foam on the strap 10m results in a secure connection between the two straps.

The strap 10m has a layer of foam 34m which engages skin 60m on body tissue 174m. The layer 34m of foam is fixedly connected to the layer 28m of fabric. The strap 10m is provided with a base end portion (not shown) corresponding to the base end portion 12 of the strap 20 (FIGS. 1, 2 and 5). In addition, the strap 10m is provided with a retainer end portion corresponding to the retainer end portion of the strap 10 (FIGS. 1, 2 and 4).

Unlike the strap 10 of FIGS. 1-5, the strap 10m (FIG. 31) is provided with a section 228 of foam which is secured to the outer side of the layer 28m of fabric. The section 228 of foam may be secured to the layer 28m of fabric in any desired manner. For example, by the use of adhesive and/or heat staking. The section 228 of foam may be provided with its own separate backing layer of fabric, that is, with a layer corresponding to the layer 28m of fabric. Alternatively, the section 228 of foam may be bonded directly to the layer 28m of fabric.

If the section 228 of foam is formed with its own backing layer of fabric, the section 228 would be connected with the strap 10m by heat staking the section of foam and its associated backing layer of fabric to the main portion 16m of the strap 10m. The backing layer of fabric connected with the section 228 of foam would be disposed in abutting engagement with the layer 228m of fabric on the main section 16m of the strap 10m. However, due to the relatively low coefficient of friction between the two layers of fabric, the section 228 of foam and its backing layer would be fixedly connected with the main portion 16m of the strap 10m by suitable fastening, such as heat staking.

In the embodiment of the invention illustrated in FIGS. 30 and 31, a second strap 224 engages the section 228 of foam on the strap 10m. However, the section 228 of foam could be disposed on the strap 10m at a location where a portion of the strap 10m is overlapped by another portion of the strap 10m. Thus, the section 228 of foam could be used to provide an anchor at an intersection between sections of a single strap 10m.

CONCLUSION

The present invention relates to a new and improved strap 10 and method of using the strap for treatment of a patient. Base and second end portions 12 and 14 of the strap 10 may be interconnected by a main portion 16 of the strap. The base end portion 12 of the strap 10 may have opposite sides 48 and 50 with surfaces which are formed of foam. The main portion 16 of the strap may have a first side 22 with a surface 31 which is formed of foam 34 and a second side 20 with a surface 26 which is formed of fabric 28. If desired, the surfaces formed of foam could be formed of a different material. A retainer 38 may be connected with the second end portion 14 of the strap 10 to connect the second end portion of the strap with the main portion 16 of the strap.

When the strap 10 is to be utilized to treat a patient, a layer 34 formed of foam disposed on the first side 22 of the strap 10 may be placed in engagement with skin 60 on the body of the patient. The base end portion 12 of the strap 10 is retained against movement relative to the body of the patient by wrapping the strap 10 around a portion of the body of the patient and positioning a portion of the layer 34 formed of foam on the first side 22 of the strap in engagement with foam disposed on the second side 20 of the base end portion 12 of the strap. The second end portion 14 of the strap 10 may be connected with a fabric layer 28 which forms the second side 20 of the strap.

If desired, a plurality of straps 10g, 120g and 136 may be utilized in the treatment of the patient. At least some of these straps 10g, 120g, and 136 may have a layer 34 of foam disposed on a first side of the strap and layer 28 of fabric disposed on the opposite side of the strap. The layers 34 of foam on the first side of the straps may be positioned in engagement with the skin of the patient and the straps may be interconnected. Interconnecting of the straps may be performed by engaging foam on the second side, that is the fabric side, of a strap with the layer of foam on the first side of a strap. A retainer 38 which, for example, may be a hook and loop type fastener, may be provided to connect an end portion of one strap with a layer 28 of fabric on another strap or with a layer of fabric on the one strap.

It is contemplated that a strap 10 constructed in accordance with the present invention may be utilized during the treatment of many different portions of a patient's body. For example, the strap may be utilized in conjunction with treatment of an arm, hand, leg, foot, shoulder, or other portion of a patient's body. A single strap 10 may be wrapped around one or more portions of a patient's body. Alternatively, a first strap 10g may be wrapped around one portion of a patient's body and a second strap 136 connected with the first strap and wrapped around another portion of a patient's body.

The strap 10 may be utilized to apply force to deep fascia such as myofascial tissue. Of course, the strap 10 may also be used to apply force to superficial fascia. It is contemplated that one or more of the straps 10 may be used to increase a patient's proprioception. The straps 10 may also be utilized to effect shifting of a bone, such as a patella, in the body of a patient. The straps 10 may be used to connect one or more treatment devices, such as a magnet, electrical stimulator, monitor, or ice pack, with a patient.

Having described the invention, the following is claimed:

1. A strap for treating a patient, the strap comprising:
a strap of material including a fabric layer and a foam layer, the fabric layer presenting an outwardly facing fabric surface and the foam layer presenting an outwardly facing foam surface, the strap having a base end portion, an opposing retainer end portion, and a main portion extending between the base end portion and the retainer end portion;
a retainer affixed to the foam surface on the retainer end portion;
wherein the retainer is releasably connectable to the outwardly facing fabric surface of the fabric layer;
wherein the base end portion includes a looped-over segment in which the material is looped over and bonded to itself such that the outwardly facing foam surface remains exposed in the looped-over segment.

2. The strap of claim 1, wherein the retainer includes a hook portion of a hook and loop fastener, and wherein the outwardly facing fabric surface includes a loop portion of the hook and loop fastener.

3. The strap of claim 1, wherein the fabric layer comprises an elasticized polymeric material.

4. The strap of claim 1, wherein the foam layer comprises an elastomeric foam.

5. The strap of claim 1, wherein the fabric layer is attached to the foam layer.

6. The strap of claim 5, wherein the fabric layer is bonded to the foam layer.

7. The strap of claim 6, wherein the foam layer is bonded to the fabric layer through an application of heat.

8. The strap of claim 7, wherein the application of heat includes an application of ultrasonic frequencies.

9. The strap of claim 1, wherein the strap is adapted to position a portion of the patient relative to an imaging device.

10. The strap of claim 9, wherein the imaging device includes a magnetic resonance imaging unit.

11. The strap of claim 1, wherein the retainer is configured to releasably couple to the outwardly facing fabric surface when the main portion is wrapped around a portion of the patient.

12. A strap for treating a portion of a patient's body, the strap comprising:
a foam layer, the foam layer being substantially elastic and including a first end and a second end;

a fabric layer, the fabric layer being substantially elastic and being secured adjacent to the foam layer, the foam layer having an elasticity greater than an elasticity of the fabric layer; and a hook fastener, the hook fastener being adjacent to the first end, the hook fastener comprising an array of hooks;

wherein the foam layer and the fabric layer form a loop at the second end.

13. The strap of claim 12, wherein the foam layer and the fabric layer are bonded together.

14. The strap of claim 13, wherein the foam layer and the fabric layer are bonded together using heat.

15. The strap of claim 13, wherein the fabric layer and the foam layer are bonded together using ultrasonic energy.

16. The strap of claim 12, wherein, in the loop at the second end, the foam layer extends around the fabric layer such that the foam layer faces outwards.

17. The strap of claim 12, wherein a magnet is secured adjacent to at least one of the foam layer and the fabric layer.

18. The strap of claim 12, wherein a medical device is secured adjacent to at least one of the foam layer and the fabric layer.

19. The strap of claim 18, wherein the medical device includes an electrical stimulator.

20. The strap of claim 18, wherein the medical device includes a monitor.

21. The strap of claim 18, wherein the medical device includes an ice pack.

22. The strap of claim 12, wherein one portion of the strap is adherent to another portion of the strap.

23. The strap of claim 12, wherein the second end contacts a portion of the body and is adherable to the surface of the body.

24. The strap of claim 12, wherein the foam layer is adapted to be placed adjacent to a surface of the patient's body; and wherein the foam layer is adherable to the surface of the patient's body.

25. The strap of claim 12, wherein the hook fastener is releasably engagable with the fabric layer.

26. The strap of claim 12, wherein the strap is adapted to move a portion of a patient's knee relative to an other portion of the patient's knee.

27. The strap of claim 26, wherein the portion of the patient's knee is a patella; an wherein the strap is adapted to move the patella into a desired position.

28. An apparatus for treating a patient, the apparatus comprising:
a strap constructed of a material including a foam layer and a fabric layer having an elasticity greater than the fabric layer, the foam layer including an outwardly facing foam surface and the fabric layer including an outwardly facing fabric surface, the strap including
an elongated main portion including a first end and a second end,
a base end portion at the first end of the main portion, the base end portion including a doubled segment of the material oriented such that both an
outermost first side and an outermost second side of the base end portion present the outwardly facing foam surface, and
a retainer end portion at the second end of the main portion, the retainer end portion including a retainer affixed to the outwardly facing foam surface, the retainer being releasably connectable to the outwardly facing fabric surface.

29. The apparatus of claim 28, wherein the segment includes a continuous section of the material that is folded back onto itself in a fabric-surface-to-fabric-surface orientation.

30. The apparatus of claim 28, wherein the segment includes a separate piece of the material affixed in a fabric-surface-to-fabric-surface orientation.

31. The apparatus of claim 28, wherein the retainer includes a hook portion of a hook and loop fastener, and wherein the fabric surface includes a loop portion of the hook and loop fastener.

32. The apparatus of claim 28, further comprising a treatment modality configured to be held in position by the strap.

33. The apparatus of claim 32, wherein the treatment modality comprises at least one magnet; wherein the fabric surface includes a loop portion of a hook and loop fastener; and wherein the magnet includes a hook portion of the hook and loop fastener.

34. The apparatus of claim 32, wherein the treatment modality comprises at least one of an electrical stimulus device, a monitor, and an ice pack.

35. The strap apparatus of claim 28, wherein the fabric layer is attached to the foam layer.

36. The strap apparatus of claim 35, wherein the fabric layer is bonded to the foam layer.

37. The apparatus of claim 28, further comprising a device adapted for at least one of straightening and correcting of at least one of a deformity or disability.

38. The apparatus of claim 28, further comprising a device adapted for at least one of fixation, union, and protection of a portion of a patient.

39. The apparatus of claim 28, further comprising a device adapted for correcting misalignment of at least one of a joint and a bone.

40. The apparatus of claim 28, wherein the strap is adapted to apply a compressive force to a portion of a patient's body.

41. An apparatus for treating a patient, the apparatus comprising:
a substantially flat, elongated strap including a first side and a second side, the strap including, in order from a first end to a second end,
a base portion,
a main portion, and
a retainer portion;
wherein the first side of the base portion and the second side of the base portion have an outer layer of foam;
wherein the first side of the main portion has an outer layer of fabric and the second side of the main portion has an outer layer of foam;
wherein the second side of the retainer portion includes a retainer, the retainer being releasably connectable to the outer layer of fabric of the first side of the main portion; and
wherein the base portion includes a laterally extending passage therethrough.

42. The apparatus of claim 41, wherein the base portion comprises a continuous section of the strap that is folded back onto itself such that the outer layer of fabric forms an inner surface of the laterally extending passage and such that an outer surface of the base portion is substantially covered by the outer layer of foam.

43. The apparatus of claim 41, wherein the retainer includes a hook portion of a hook and loop fastener, and wherein the outer layer of fabric includes a loop portion of the hook and loop fastener.

44. The apparatus of claim 41, further comprising a treatment modality configured to be held in position by the strap; wherein the treatment modality comprises at least one of a magnet, an electrical stimulus device, a monitor, and an ice pack.

45. The apparatus of claim 41, further comprising a device adapted for at least one of straightening and correcting of at least one of a deformity or disability.

46. The apparatus of claim 41, further comprising a device adapted for at least one of fixation, union, and protection of a portion of the patient.

47. The apparatus of claim 41, further comprising a device adapted for correcting misalignment of at least one of a joint and a bone.

48. The apparatus of claim 41, wherein the strap is adapted to apply a force to myofascial tissue.

49. The apparatus of claim 41, wherein the strap is adapted to apply a force to superficial fascia.

50. The apparatus of claim 41, wherein the strap is adapted to increase a patient's propioception.

* * * * *